(12) United States Patent
Bhagavatula et al.

(10) Patent No.: US 9,638,862 B2
(45) Date of Patent: *May 2, 2017

(54) MONOLITHIC BEAM-SHAPING OPTICAL SYSTEMS AND METHODS FOR AN OCT PROBE

(71) Applicant: Corning Incorporated, Corning, NY (US)

(72) Inventors: Venkata Adiseshaiah Bhagavatula, Big Flats, NY (US); Klaus Hartkorn, Painted Post, NY (US); Daniel Max Staloff, Rochester, NY (US)

(73) Assignee: Corning Incorporated, Corning, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/688,112

(22) Filed: Apr. 16, 2015

(65) Prior Publication Data

US 2015/0219854 A1 Aug. 6, 2015

Related U.S. Application Data

(63) Continuation of application No. 13/827,234, filed on Mar. 14, 2013, now Pat. No. 9,036,966.

(Continued)

(51) Int. Cl.
 *G02B 6/32* (2006.01)
 *A61B 5/00* (2006.01)
 *G01B 9/02* (2006.01)

(52) U.S. Cl.
 CPC .............. *G02B 6/32* (2013.01); *A61B 5/0066* (2013.01); *G01B 9/0205* (2013.01);
 (Continued)

(58) Field of Classification Search
 CPC ........... G02B 6/32; G02B 6/322; G02B 6/241
 (Continued)

(56) References Cited

U.S. PATENT DOCUMENTS

| 5,321,501 A | 6/1994 | Swanson et al. |
| 6,069,698 A | 5/2000 | Ozawa et al. |

(Continued)

FOREIGN PATENT DOCUMENTS

| CA | 2414795 | 6/2004 |
| CN | 202010139 U | 10/2011 |

(Continued)

OTHER PUBLICATIONS

Edmund Optics—Ball Lens, hemispherical lens Drum Lens literature: publications and company brochures that sell these products. http://www.edmundoptics.com/search/index.cfm?criteria=ball+lenses.

(Continued)

*Primary Examiner* — Rhonda Peace
(74) *Attorney, Agent, or Firm* — Svetlana Z. Short

(57) ABSTRACT

Monolithic beam-shaping optical systems and methods are disclosed for an optical coherence tomography (OCT) probe that includes a transparent cylindrical housing having asymmetric optical power. The system includes a transparent monolithic body having a folded optical axis and at least one alignment feature that supports the end of an optical fiber adjacent an angled planar end wall. The monolithic body also includes a total-internal reflection surface and a lens surface that define object and image planes. Light from the optical fiber end traverses the optical path, which includes the cylindrical housing residing between the lens surface and the image plane. Either the lens surface by itself or the lens surface and the reflective (eg, TIR) surface in combination are configured to substantially correct for the asymmetric (Continued)

optical power of the cylindrical housing, thereby forming a substantially rotationally symmetric image spot at the image plane.

22 Claims, 16 Drawing Sheets

Related U.S. Application Data

(60) Provisional application No. 61/616,734, filed on Mar. 28, 2012.

(52) U.S. Cl.
CPC ..... *G01B 9/02034* (2013.01); *G01B 9/02035* (2013.01); *G01B 9/02091* (2013.01); *Y10T 29/4978* (2015.01)

(58) Field of Classification Search
USPC .................................................. 385/33–35
See application file for complete search history.

(56) References Cited

U.S. PATENT DOCUMENTS

| | | | |
|---|---|---|---|
| 6,134,003 A | 10/2000 | Tearney et al. | |
| 6,327,493 B1 | 12/2001 | Ozawa et al. | |
| 6,445,939 B1 | 9/2002 | Swanson et al. | |
| 6,501,878 B2 | 12/2002 | Hughes et al. | |
| 6,564,087 B1 | 5/2003 | Pitris et al. | |
| 6,891,984 B2 | 5/2005 | Petersen et al. | |
| 6,904,197 B2 | 6/2005 | Bhagavatula et al. | |
| 7,228,033 B2 | 6/2007 | Bhagavatula et al. | |
| 7,241,286 B2 | 7/2007 | Atlas | |
| 7,258,495 B1 | 8/2007 | Hughes, Jr. et al. | |
| 7,366,376 B2 | 4/2008 | Shishkov et al. | |
| 7,679,754 B2* | 3/2010 | Zuluaga ............... | A61B 5/0066 356/451 |
| 7,940,397 B2 | 5/2011 | Masuda | |
| 7,944,556 B2 | 5/2011 | Smous et al. | |
| 7,952,718 B2 | 5/2011 | Li et al. | |
| 8,054,469 B2* | 11/2011 | Nakabayashi ....... | A61B 5/0066 356/479 |
| 8,169,618 B2 | 5/2012 | Inoue | |
| 8,186,109 B2 | 5/2012 | Warminsky | |
| 8,369,663 B2 | 2/2013 | Juni et al. | |
| 8,515,221 B2* | 8/2013 | Flanders ............ | G02B 23/2469 385/31 |
| 8,675,293 B2 | 3/2014 | Flanders et al. | |
| 8,857,220 B2 | 10/2014 | Bhagavatula et al. | |
| 8,861,900 B2 | 10/2014 | Bhagavatula et al. | |
| 8,964,017 B2* | 2/2015 | Vertikov ............... | A61B 5/0066 348/65 |
| 8,967,885 B2 | 3/2015 | Bhagavatula et al. | |
| 9,036,966 B2* | 5/2015 | Bhagavatula ............ | G02B 6/32 385/33 |
| 2002/0197020 A1 | 12/2002 | Qian et al. | |
| 2003/0021543 A1 | 1/2003 | Mann et al. | |
| 2003/0142934 A1 | 7/2003 | Pan et al. | |
| 2005/0201662 A1 | 9/2005 | Petersen et al. | |
| 2006/0067620 A1 | 3/2006 | Shishkov et al. | |
| 2008/0228033 A1 | 9/2008 | Tumlinson et al. | |
| 2009/0190833 A1 | 7/2009 | Alvino et al. | |
| 2009/0190883 A1 | 7/2009 | Kato et al. | |
| 2009/0198125 A1 | 8/2009 | Nakabayashi et al. | |
| 2009/0244545 A1 | 10/2009 | Toida | |
| 2010/0014052 A1 | 1/2010 | Koschmieder et al. | |
| 2010/0253949 A1 | 10/2010 | Adler et al. | |
| 2011/0122410 A1 | 5/2011 | Wang et al. | |
| 2011/0182550 A1* | 7/2011 | Flanders ............ | G02B 23/2469 385/50 |
| 2011/0206838 A1 | 8/2011 | Juni et al. | |
| 2011/0218403 A1* | 9/2011 | Tearney ............... | A61B 5/0066 600/165 |
| 2012/0052565 A1 | 3/2012 | DeRosa et al. | |
| 2013/0266259 A1 | 10/2013 | Bhagavatula et al. | |
| 2014/0066756 A1* | 3/2014 | Sinclair ............... | A61B 5/0077 600/427 |
| 2015/0025369 A1* | 1/2015 | Bhagavatula ........ | G01B 9/0205 600/425 |
| 2015/0036146 A1* | 2/2015 | Staloff ............... | G01B 9/02091 356/479 |
| 2015/0146211 A1* | 5/2015 | Bhagavatula ........ | A61B 5/0066 356/479 |
| 2015/0219854 A1* | 8/2015 | Bhagavatula ............ | G02B 6/32 385/33 |

FOREIGN PATENT DOCUMENTS

| | | |
|---|---|---|
| EP | 0575993 | 12/1993 |
| EP | 2133781 | 12/2009 |
| JP | 1156786 A | 6/1989 |
| JP | 2008188081 A | 8/2008 |
| WO | 00/58766 | 10/2000 |
| WO | 01/11409 | 2/2001 |
| WO | 2009/066969 | 5/2009 |
| WO | 2011/069630 | 6/2011 |
| WO | 2011/091408 | 7/2011 |

OTHER PUBLICATIONS

Xi, Huo, et al., "High Resolution OCT balloon imaging catheter with astigmatism correction", Optic Letters, vol. 34, No. 13, p. 1943-1945 (Jul. 1, 2009).

Cabibihan, J-J et al., "Prosthetic finger phalanges with lifelike skin compliance for low-force social touching interactions", Journal of NeuroEngineering and Rehabilitation 2011, 8:16.

Cabibihan, J-J et al., "Towards Humanlike Social Touch for Sociable Robitics and Prosthetics: Comparisons on the Compliance, Conformance and Hysteresis of Synthetic and Human Fingertip Skins", International Journal of Social Robotics, vol. 1, Issue 1, pp. 29-40 (2009).

May 16, 2013 International Search Report and Written Opinion issued in related application PCT/2013/026989.

May 21, 2013 International Search Report and Written Opinion issued in related application PCT/US2013/026986.

Australian Patent Examination Report No. 1 AU2013239826 Dated Jul. 24, 2016.

Chinese First Office Action CN201380027832.6 Dated May 15, 2016.

International Search Report and Written Opinion PCT/US2013/026987 Dated Jul. 19, 2013.

International Search Report and Written Opinion PCT/US2013/033990 Dated Jul. 29, 2013.

* cited by examiner

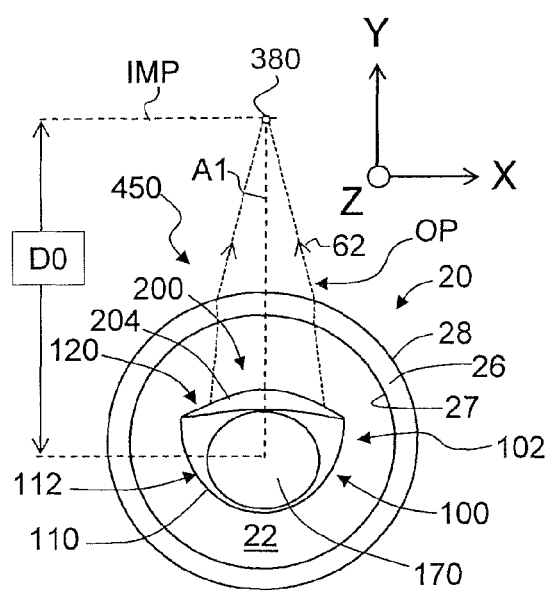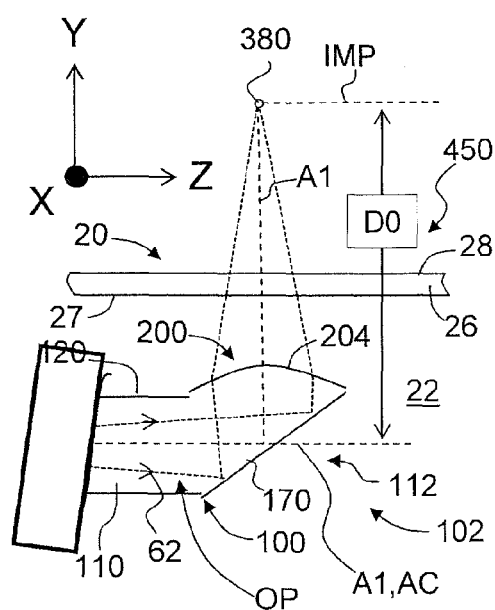
FIG. 11  FIG. 12

MONOLITHIC BEAM-SHAPING OPTICAL SYSTEMS AND METHODS FOR AN OCT PROBE

CROSS-REFERENCE TO RELATED APPLICATIONS

This application is a continuation of and claims the benefit of priority to U.S. patent application Ser. No. 13/827,234 filed on Mar. 14, 2013 which claims the benefit of priority under 35 U.S.C. 119 of U.S. Provisional Application Ser. No. 61/616,734 filed on Mar. 28, 2012 the content of which is relied upon and incorporated herein by reference in its entirety.

FIELD

The present disclosure relates to optical coherence tomography (OCT), and in particular to a monolithic beam-shaping optical system for an OCT probe.

BACKGROUND ART

Optical coherence tomography (OCT) is used to capture a high-resolution cross-sectional image of scattering biological tissues and is based on fiber-optic interferometry. An example OCT system is described in U.S. Pat. No. 5,321,501 and U.S. Patent Application Publication No. 2009/0198125 which are incorporated by reference herein in its entirety. The core of an OCT system is a Michelson interferometer, wherein a first optical fiber is used as a reference arm and a second optical fiber is used as a sample arm. The sample arm includes the sample to be analyzed, as well as a small probe that contains small optical components therein. An upstream light source provides the imaging light. A photodetector is arranged in the optical path downstream of the sample and reference arms. The probe is used to direct light into or onto the sample and then to collect scattered light from the sample.

Optical interference of light from the sample arm and the reference arm is detected by the photodetector only when the optical path difference between the two arms is within the coherence length of the light from the light source. Depth information from the sample is acquired by axially varying the optical path length of the reference arm and detecting the interference between light from the reference arm and scattered light from the sample arm. A three-dimensional image is obtained by transversely scanning in two dimensions the optical path in the sample arm. The axial/depth resolution of the process is determined by the coherence length, while the overall transverse resolution is dictated by the size of the image spot formed by the optical components of the probe.

Because the probe typically needs to be inserted into a small cavity of the body, it must be small and preferably have a simple optical design. Example designs for the probe include a transparent cylinder in which the miniature probe optical components are contained and through which light is transmitted and received. However, the curved body of the transparent cylinder induces optical aberrations that, if uncorrected, can degrade the image quality to the point where the image is useless. Moreover, having multiple and separate optical components in the probe is problematic because the small optical components have to be assembled and aligned, which adds to the cost and complexity of manufacturing the probe.

SUMMARY

An aspect of the disclosure is a beam-shaping optical system that supports an optical fiber having a central axis and an end, with the system being suitable for use within an optical coherence tomography (OCT) transparent housing having a cylindrical body with asymmetric optical power. The beam-shaping optical system includes a transparent monolithic body having an optical axis, an outer surface and opposite front and back ends. The system also includes, in order along the optical axis, at least one alignment feature, a recess, an angled planar end wall, a reflective surface (for example a total-internal reflection (TIR) surface), and a lens surface. The at least one alignment feature is configured to operably support the optical fiber so that the optical fiber central axis is substantially coaxially aligned with the optical axis. The recess terminates the at least one alignment feature at the angled planar end wall. The reflective surface (eg, TIR) is located at the front end and forms the folded optical axis. The lens surface is integrally formed in the monolithic body along the folded optical axis and constitutes part of the outer surface adjacent the front end. The beam-shaping system has optical power, which is provided in one of two ways: a) only the lens surface has optical power and is configured to substantially compensate for the asymmetric optical power of the OCT transparent housing; or b) the lens surface and reflective surface (eg, TIR) each have optical power and are cooperatively configured to substantially compensate for the asymmetric optical power of the OCT transparent housing.

Another aspect of the disclosure is an optical assembly that includes the beam-shaping optical system as described above, and also includes the optical fiber, wherein the optical fiber is operably supported by the at least one alignment feature.

Another aspect of the disclosure is a beam-shaping optical system that supports an optical fiber and that is for use within a transparent cylindrical housing that has asymmetric optical power. The system has a transparent monolithic body having a substantially uniform refractive index at an infrared operating wavelength, a folded optical axis, a top, a front end, a back end and an outer surface, The outer surface has at least one flat surface that is formed in the top and that is adjacent the back end. The system includes at least one alignment feature integrally formed in the at least one flat surface of the monolithic body and configured to support and align the optical fiber. The at least one alignment feature terminates at an angled planar end wall that defines a first optical surface. The system also has a recess formed in the optical fiber alignment feature adjacent the angled planar end wall. The system further includes a reflective surface, for example a TIR surface, which is planar surface integrally formed in the monolithic body at the front end and along the optical axis. The reflective planar surface is angled relative to the optical axis and defines a second optical surface that forms the folded optical axis. The system also has a lens surface formed at the top of the monolithic body adjacent the front end and along the folded optical axis. The lens surface constitutes part of the outer surface and defines a third optical surface. The lens surface has an anamorphic aspherical shape and defines an optical power for the beam-shaping optical system. The lens surface is configured to substantially compensate for the asymmetric optical power of the cylindrical housing.

Another aspect of the disclosure is a beam-shaping optical assembly that includes the beam-shaping optical system as described above and the optical fiber. The optical fiber is supported by the at least one alignment feature. The optical fiber has an end that resides adjacent the angled planar end wall and at an object plane defined by the lens surface. The optical fiber end can be angled in a manner that reduces the adverse effects of reflections, such as reflections from the angled planar end wall that could then reflect from the optical fiber end and then travel back through the angled planar end wall.

Another aspect of the disclosure is a method of forming an image spot through a cylindrical transparent housing having asymmetric optical power with light from an optical fiber having an end and a central axis. The method includes operably supporting the optical fiber in at least one alignment feature of a transparent monolithic body having an outer surface and that is configured to define a folded optical path along a folded optical axis from an angled planar end wall to a reflective surface (for example a TIR surface) and then to a lens surface. Either the lens surface or the lens surface and the reflective surface define an object plane at which the optical fiber end resides and also define an image plane where the image spot is formed. The lens surface constitutes part of the outer surface, with either the lens surface or both the lens surface and the reflective surface (eg, TIR surface) being configured to substantially compensate for the asymmetric optical power of the cylindrical transparent housing, which lies in the optical path between the lens surface and the image plane. The method also includes sending light from the optical fiber end at the object plane through the angled planar end wall and over the folded optical path to the image plane to form a substantially rotationally symmetric image spot at the image plane.

Another aspect of the disclosure is an OCT system. The OCT system includes an OCT probe that includes the beam-shaping optical system disclosed herein. The OCT system also includes a light source that emits light coherent light. The OCT system further includes an interferometer optically coupled to the light source. The interferometer has a reference arm and a sample arm. The sample arm includes the OCT probe. The interferometer is configured to cause light to travel over both the sample and reference arms and to form interfered light. The OCT system also has a photodetector configured to receive and detect the interfered light and to generate an electrical signal in response thereto. The OCT system also has a computer configured to receive and process the electrical signal.

It is to be understood that both the foregoing general description and the following Detailed Description represent embodiments of the disclosure, and are intended to provide an overview or framework for understanding the nature and character of the disclosure as it is claimed. The accompanying drawings are included to provide a further understanding of the disclosure, and are incorporated into and constitute a part of this specification. The drawings illustrate various embodiments of the disclosure and together with the description serve to explain the principles and operations of the disclosure.

Additional features and advantages of the disclosure are set forth in the Detailed Description that follows, and in part will be readily apparent to those skilled in the art from that description or recognized by practicing the disclosure as described herein, including the Detailed Description that follows, the claims, and the appended drawings.

The claims are incorporated into and constitute part of the Detailed Description set forth below.

Any numerical ranges provided herein are inclusive of the limits used unless otherwise stated.

BRIEF DESCRIPTION OF THE DRAWINGS

FIG. 11 is a cross-sectional view of the OCT probe of FIG. 10 as viewed in the X-Y plane and shows the formation of the image spot at the image plane;

FIG. 12 is a cross-sectional view of the OCT probe of FIG. 10 as viewed in the Y-Z plane and shows the formation of the image spot at the same image plane as for the X-Y plane;

Figure 1:
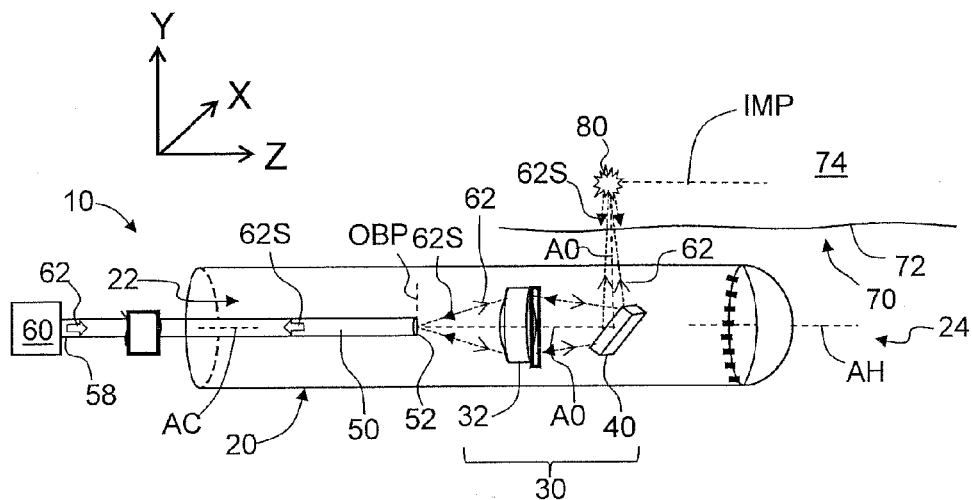
FIG. 1 is a perspective view of a generalized prior art OCT probe and optical system.

Additional features and advantages of the disclosure are set forth in the Detailed Description that follows and will be apparent to those skilled in the art from the description or recognized by practicing the disclosure as described herein, together with the claims and appended drawings. It will be understood that the illustrations are for the purpose of describing particular embodiments and are not intended to limit the disclosure or the appended claims. The drawings are not necessarily to scale, and certain features and certain views of the drawings may be shown exaggerated in scale or in schematic in the interest of clarity and conciseness.

Cartesian coordinates are shown in certain of the Figures for the sake of reference and are not intended as limiting with respect to direction or orientation.

DETAILED DESCRIPTION

In the following description, like reference characters designate like or corresponding parts throughout the several views shown in the figures.

The mode field diameter MFD is a measure of the spot size or beam width of light propagating in a single mode fiber or at another location in an optical system. The mode field diameter MFD within an optical fiber is a function of the source wavelength, fiber core radius r and fiber refractive index profile. In an example, the mode field diameter MFD can be measured as the full width at 13.5% of the peak power for a best fit Gaussian beam, while in another example it can be measured using the Peterman II method, where MFD=2w, and $$w^2 = 2 \frac{\int_0^\infty E^2 r dr}{\int_0^\infty (dE/dr)^2 r dr},$$

wherein E is the electric field distribution in the optical fiber and r is the radius of the optical fiber core.

With reference to the Figures discussed in greater detail below, the mode field diameter MFD is also referred to herein as a property of an image spot 380, in which case it is referred to as the "image mode field diameter $MFD_{IM}$," or "image $MFD_{IM}$" for short. Likewise, the mode field diameter MFD associated with an optical fiber 50 at an optical fiber end 52 is referred to as "the fiber mode field diameter $MFD_F$," or "fiber $MFD_F$" for short.

FIG. 1 is an elevated view of a generalized conventional prior art OCT probe 10. The OCT probe 10 includes a generally cylindrical (i.e., tube-like) housing 20 having a central axis AH, an interior 22, a rounded front end 24 and a curved body 26 having curved inner and outer surfaces 27 and 28 (see FIG. 2 and FIG. 3). The housing 20 is substantially transparent to the OCT operating wavelength λ. In an example, housing 20 is formed from a section of capillary tubing. Materials for housing 20 include glass and plastic.

The housing interior 22 is configured to contain a beam-shaping optical system 30 that includes an imaging lens 32 and a fold mirror 40 disposed along an optical axis A0, which in an example is either substantially co-linear with or offset but parallel to housing central axis AH. The imaging lens 32 defines an object plane OBP and an image plane IMP. The OCT probe 10 includes an optical fiber 50 that has a central axis AC and an end 52 that resides at object plane OBP. The optical fiber end 52 can be "flat," or "non-angled," i.e., it can define a planar surface that is 90° relative to optical fiber central axis AC, or it can be angled, i.e., it can define a planar surface that is other than 90° relative to optical fiber central axis AC. In an example, optical fiber end 52 is angled with the same angle θ1 of a planar end wall 160, as introduced and described below (see e.g., FIG. 6A). The optical fiber end 52 can be angled in the same direction or the opposite direction as angle θ1 of planar end wall 160.

The optical fiber 50 also has an end 58 that is opposite to end 52 and that is optically coupled to a light source 60 that emits light 62 of the operating wavelengths λ. The OCT probe 10 is shown relative to a sample 70 that includes a surface 72 and a body 74. The sample 70 may be, for example, a biological sample, such as human or animal tissue. The combination of beam-shaping optical system 30 and optical fiber 50 forms a beam-shaping optical assembly.

In the ideal operation of OCT probe 10, light 62 from light source 60 travels down optical fiber 50 and is emitted as a diverging light at optical fiber end 52. The imaging lens 32 collects diverging light 62 and forms converging light 62, which is directed along optical axis A0 to fold mirror 40. The fold mirror 40 directs converging light 62 along folded optical axis A0 to image plane IMP, where the converging light forms an image spot 80.

The formation of image spot 80 within sample body 74 gives rise to scattered light 62S from the sample body, which returns generally along the same optical path as that light of light 62 that forms the image spot. In particular, the collected scattered light 62S is imaged onto optical fiber end 52 by imaging lens 32, and thereby the collected scattered light is optically coupled into optical fiber 50. This scattered light 62S is then carried by optical fiber 50 and is ultimately diverted to a different optical fiber (not shown) before it reaches light source 60. This collected scattered light 62S is then interfered with light from the reference arm (not shown) of the OCT system and the interfered light is detected and used to form an OCT image of the illuminated portion of sample 70.

Figure 2:
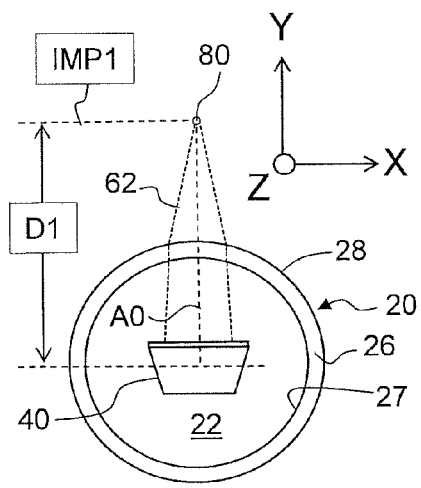
FIG. 2 is a cross-sectional view of the OCT probe of FIG. 1 as viewed in the X-Y plane and FIG. 3 is a cross-sectional view of the OCT probe of FIG. 1 as viewed in the Y-Z plane.
Figure 3:
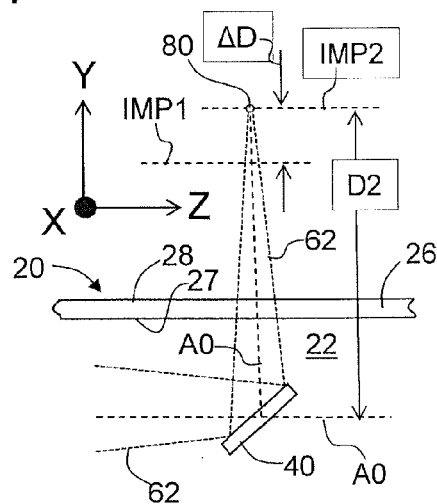

FIG. 2 is a cross-sectional view of OCT probe 10 of FIG. 1 as viewed in the X-Y plane, while FIG. 3 is a cross-sectional view of the OCT probe of FIG. 1 as viewed in the Y-Z plane. FIGS. 2 and 3 illustrate a phenomenon whereby the curved body 26 of housing 20 as defined by inner and outer surfaces 27 and 28 acts as a cylindrical lens that has optical power in the X-Y plane but no optical power in the Y-Z plane (i.e., has asymmetrical optical power). This serves to create two image planes, namely, IMP1 and IMP2, that are different distances D1 and D2 away from the horizontal portion of optical axis A0 and so are axially displaced from one another by a distance AD. The result is that image spot 80 is not tightly focused, which prevents collected scattered light 62S from forming a useful OCT image.

Moreover, beam-shaping optical system 30 includes discrete optical components (namely, lens 32 and fold mirror 40) that are very small (e.g., less than 1 mm in diameter) and that need to be aligned with one another as well as with optical fiber 50. This, as mentioned above, makes conventional OCT probes 10 difficult and costly to manufacture.

Beam-Shaping Optical System

Figure 4A:
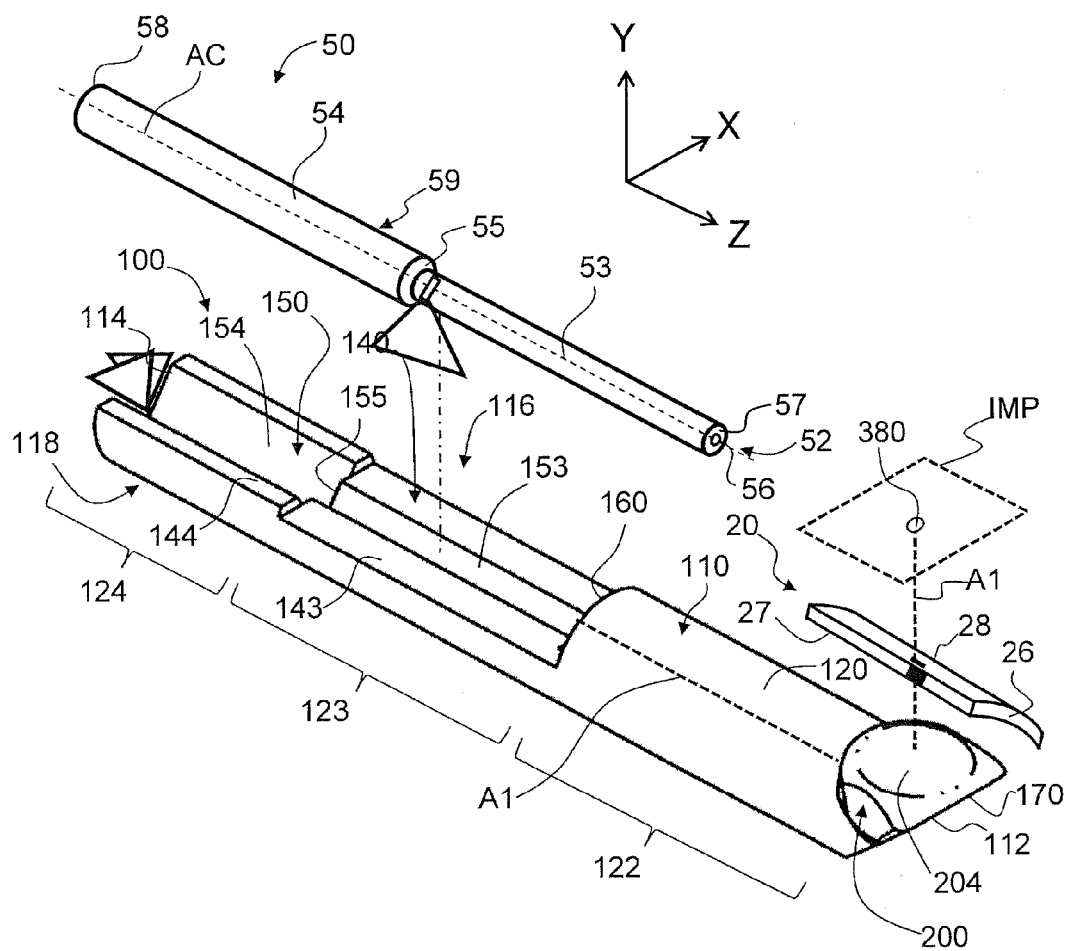
FIG. 4A is an elevated view of an example beam-shaping optical system for use in forming an OCT probe, along with an example optical fiber suitable for use with the beam-shaping optical system.
Figure 4B:
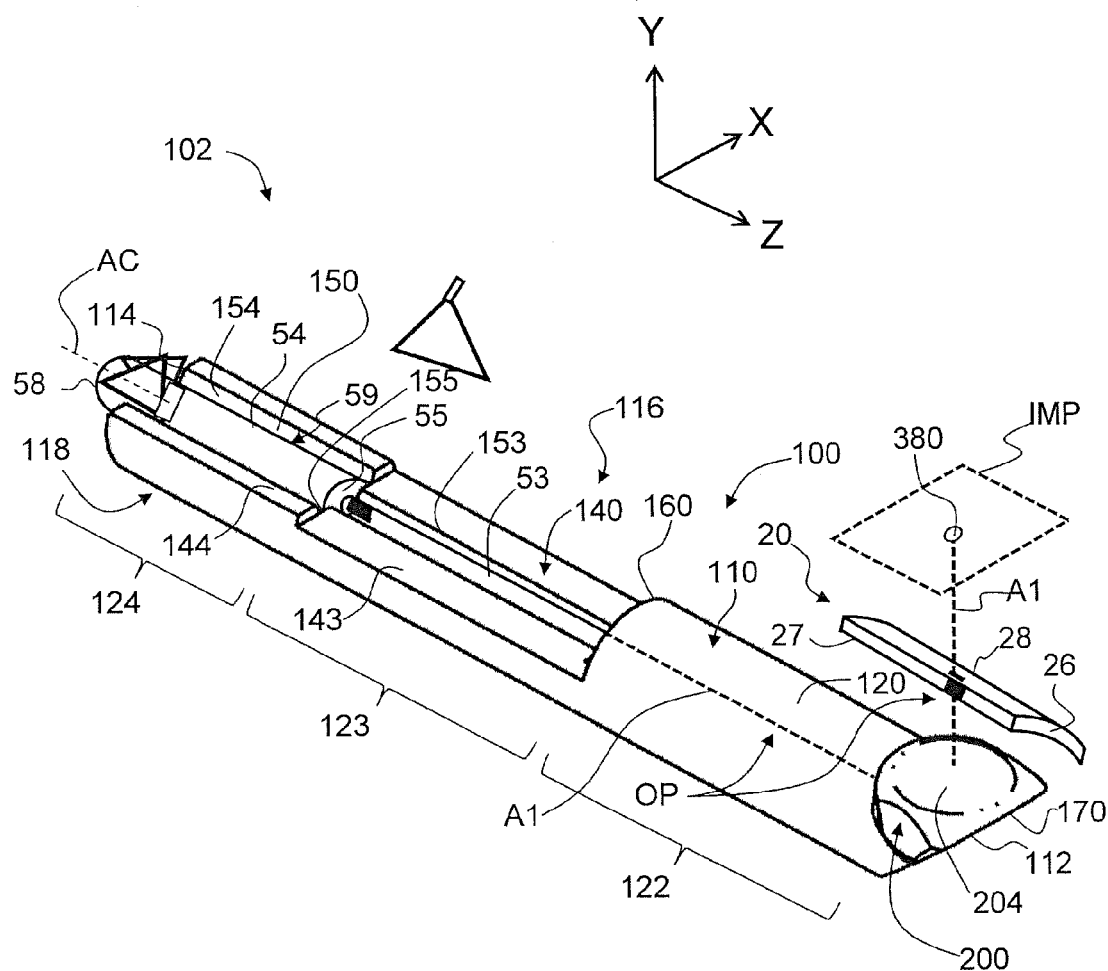
FIG. 4B is the same as FIG. 4A, except that the optical fiber is operably supported by the beam-shaping optical system to form a beam-shaping optical assembly.
Figure 5A:
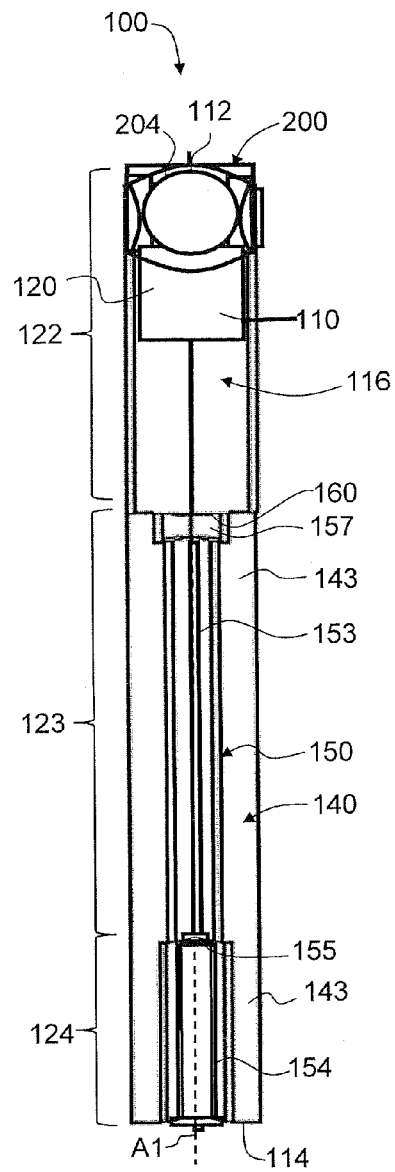
FIG. 5A and FIG. 5B are top-down views of the beam-shaping optical system without optical fiber in place (FIG. 5A) and with the optical fiber in place (FIG. 5B) to form the beam-shaping optical assembly.
Figure 5B:
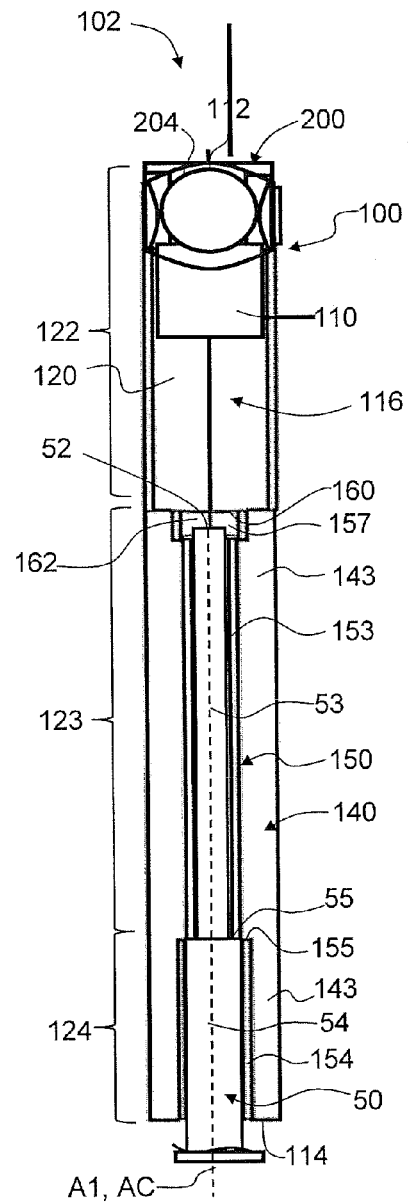
Figure 6A:
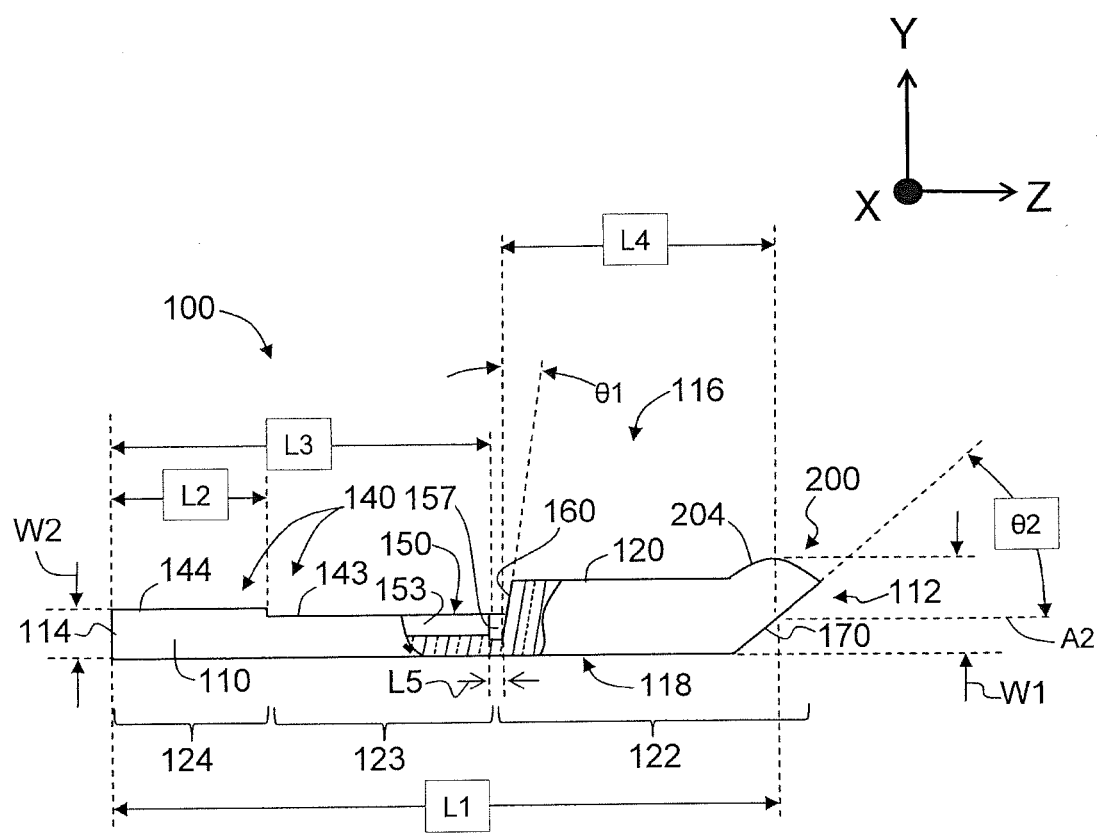
FIG. 6A is a side view of the beam-shaping optical system that includes a cut-away portion in the central section and that shows a number of different dimensions.
Figure 6B:
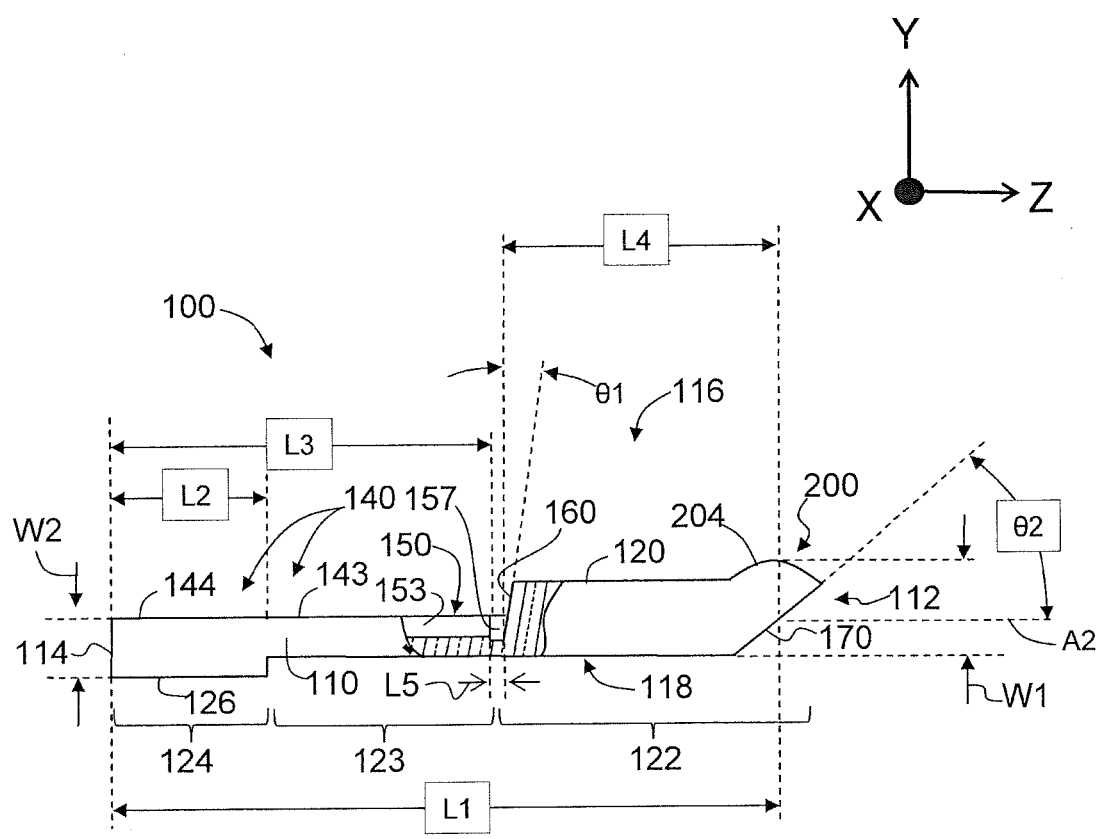
FIG. 6B is similar to FIG. 6A and illustrates an embodiment for the beam-shaping optical system wherein the first and second flat surface portions lie in the same plane, and wherein the bottom surface includes a lip adjacent the back end.
Figure 6C:
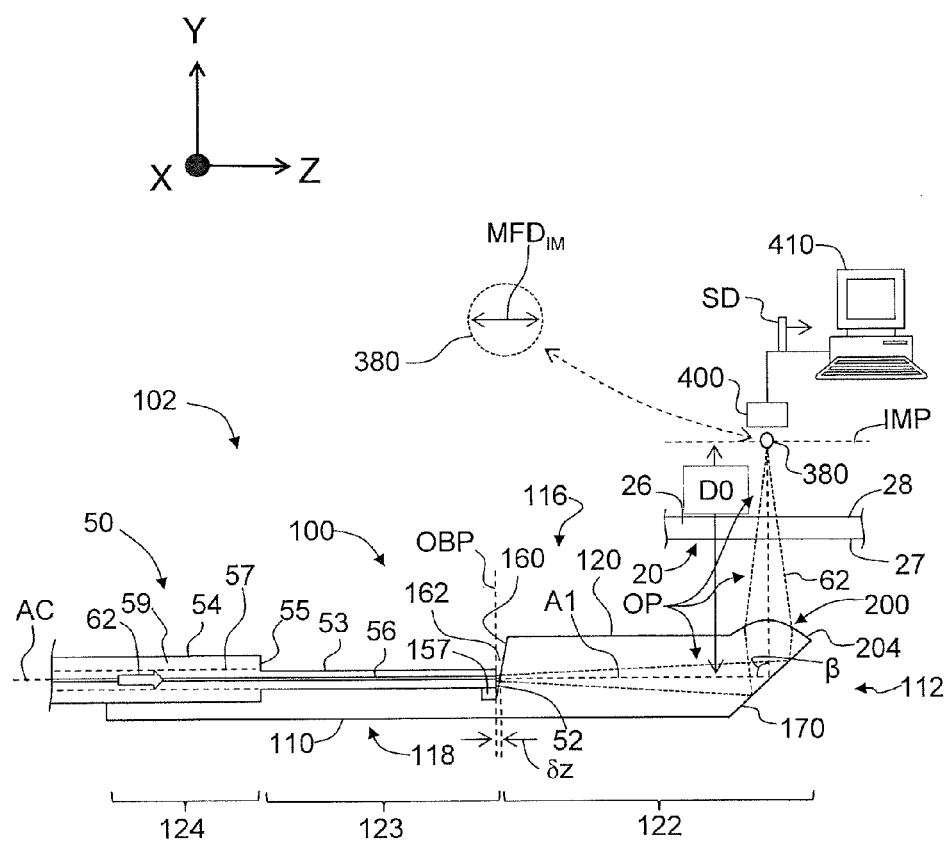
FIG. 6C is a cross-sectional view of the beam-shaping optical system taken in the Y-Z plane, with the optical fiber in place to form the beam-shaping optical assembly.
Figure 6D:
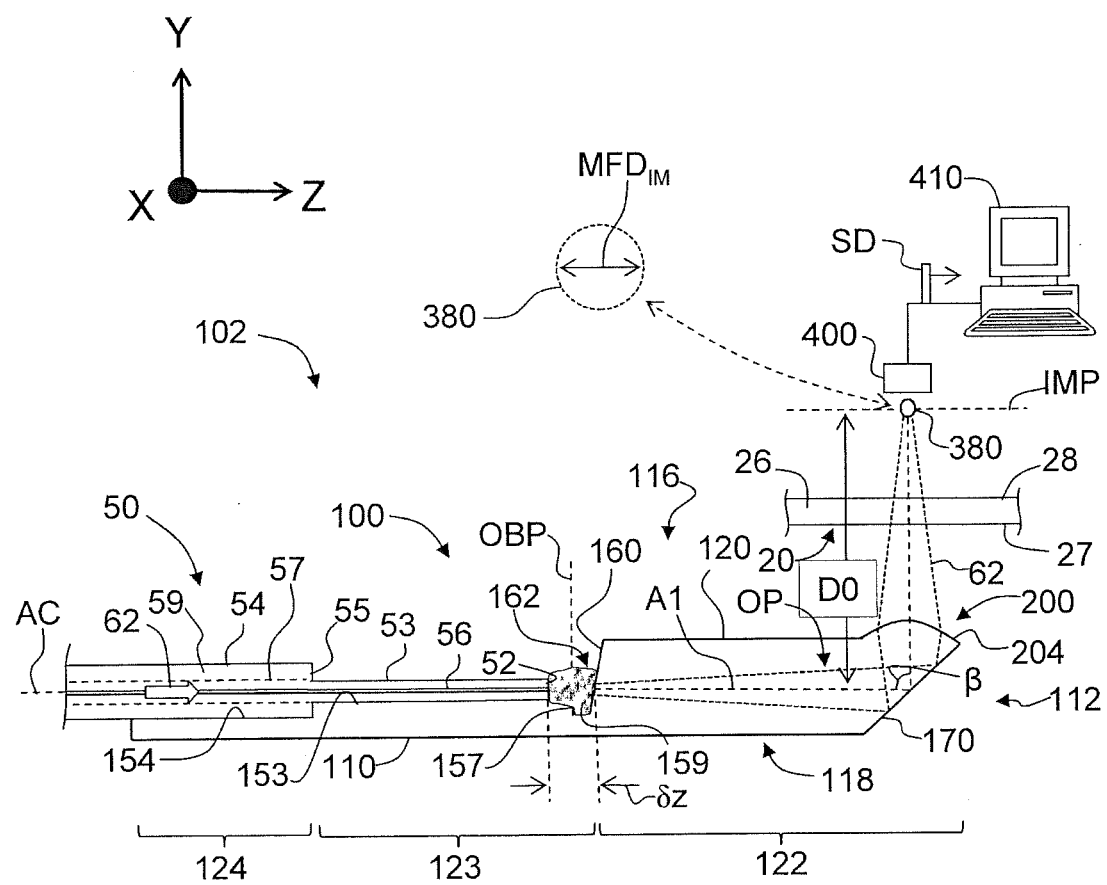
FIG. 6D is essentially the same as FIG. 6C except that the axial distance δz between the optical fiber end and the adjacent planar end wall is greater than that shown in FIG. 6C.

FIG. 4A is an elevated view of an example beam-shaping optical system ("system") 100 for use in forming an OCT probe, along with an example of optical fiber 50 suitable for use with the system. FIG. 4B is the same as FIG. 4A, except that optical fiber 50 is operably supported by system 100 to form a beam-shaping optical assembly ("assembly") 102. FIG. 5A and FIG. 5B are top-down views of system 100 (FIG. 5A), and the corresponding assembly 102 (FIG. 5B). FIG. 6A and FIG. 6B are side views of different examples of system 100 that include a central cut-away portion and that show a number of different dimensions, while FIGS. 6C and 6D are cross-sectional views taken in the Y-Z plane of the corresponding assembly 102.

The optical fiber 50 as used in system 100 to form assembly 102 has a coated section 54 and an uncoated section 53, with the uncoated section having the aforementioned optical fiber end 52 and central axis AC. Shown in FIG. 4A, at optical fiber end 52 is a core 56 surrounded by a cladding 57. In coated section 54, cladding 57 is surrounded by at least one buffer layer 59, which is stripped off to form uncoated (i.e., unbuffered) section 53. The boundary between coated section 54 and uncoated section 53 is defined by a coated-section edge 55.

With reference to FIG. 4A through FIG. 6B, system 100 includes an optical axis A1 that runs in the Z-direction and that is folded as described below by an angle β. The angle β need not be limited to 90°, and in an example can vary by 10° on either side of 90°. The system 100 consists of a monolithic body 110. In an example, monolithic body 110 is made of a polymer material that is capable of being molded and that is transparent to light 62 having the operating wavelength λ. In another example embodiment, monolithic body 112 is made of a glass material ("glass") that is transparent to light 62 having the operating wavelength λ. It is noted that the term "transparent" as used herein not limited to the concept of perfect or ideal transparency, and includes the concept of the material being "substantially transparent."

In an example, the operating wavelength λ includes an infrared wavelength such as one in the range from 1,000 nm to 1,600 nm, with exemplary operating wavelengths being about 1300 nm and about 1560 nm.

An exemplary polymer material for forming monolithic body 110 has a relatively low birefringence. Exemplary materials for monolithic body 110 include ZEONOR® (available from Zeon Chemicals L.P., Louisville, Ky.) and polyetherimide (PEI), which is a thermoplastic material. Other plastics and polymers can be used as well, as will be understood by one skilled in the art. The ability to form system 100 as a monolithic structure via a mold process provides a low-cost manufacturing solution for OCT probes.

In an example embodiment, monolithic body 110 is made by micromachining a precision mold and then using a suitable material, such as one of the example materials mentioned above, to perform a molding process using the micromachined mold and related techniques known in the art.

The monolithic body 110 includes a front end 112, a back end 114, a top 116, a bottom 118, and an outer surface 120. For convenience, monolithic body 110 can be considered to be three main sections, namely a front section 122 adjacent front end 112, a central section 123 in between the front end and back end 114, and a back section 124 adjacent the back end. An example monolithic body 110 is generally cylindrical with a rounded cross-sectional shape and has a number of functional features formed therein. In an example, monolithic body 110 is substantially homogenous with a substantially constant index of refraction at the operating wavelength λ. In particular, monolithic body 110 does not have any substantial index of refraction gradient and ideally has a constant refractive index at the operating wavelength λ. Thus, no substantial optical power originates within monolithic body by virtue of a substantial refractive index gradient, such as those associated with gradient-index lenses.

The monolithic body outer surface 120 includes at least one flat surface 140 that has at least one alignment feature 150 integrally formed therein. The at least one alignment feature 150 is configured to operably support optical fiber 50 when the optical fiber is disposed therein such that optical fiber central axis AC co-axially aligns with optical axis A1. An optical path OP is folded and is generally centered on optical axis A1.

In an exemplary embodiment, the at least one flat surface 140 includes in central section 123 a first flat surface portion 143 that resides in an X-Z plane. The first flat surface portion 143 includes a first central alignment feature 153 formed therein. Further in the example, the at least one flat surface 140 includes in back section 124 a second flat surface portion 144 that also resides in an X-Z plane but that is offset slightly in the +Y direction relative to first flat surface portion 143, i.e., second flat surface portion 144 is slightly higher in the Y-direction than is first flat surface portion 143 (see FIG. 6). Thus, second flat surface portion 144 can be said to be elevated relative to first flat surface portion 143. In an example embodiment as shown in FIG. 6B, there is no height difference (i.e., no offset) between first and second flat surface portions 143 and 144. Also, in an example, system 100 includes a lip 126 formed in bottom surface 118 adjacent back end 114. The lip 126 facilitates handling of system 100, e.g., mounting the system onto a support fixture when the system is incorporated into an OCT probe, as described in greater detail below.

The second flat surface portion 144 includes a second central alignment feature 154 that is formed therein and that is open to and aligned with the first central alignment feature 153. In an exemplary embodiment, second central alignment feature 154 is wider than first central alignment feature 153, which serves to define an alignment feature edge 155 between the two adjacent alignment features and against which coated-section edge 55 butts when optical fiber 50 is operably arranged in the first and second alignment features. This assists in optical fiber 50 being properly disposed in and supported by monolithic structure 110 and also serves to keep the optical fiber in place within the first and second alignment features 153 and 154.

In an example, first and second central alignment features 153 and 154 each comprise grooves, which in an example are aligned and have a generally V-shaped, truncated V-shaped or U-shaped cross-section. In an example, the grooves have different sizes, with the groove closest to the back end being the widest. First and second flat surface portions 143 and 144 facilitate handling of system 100, e.g., they can be used to clamp onto to steady monolithic body 110 during alignment or during assembly of an OCT probe.

In one example, first central alignment feature 153 has a more rounded cross-sectional shape (e.g., a U-shape) than the second central alignment feature 154 to provide strain relief to an optical fiber, as described below. Another advantage of a rounded cross-sectional shape is that it is easier to form using a molding process because the portion of the mold that forms the rounded alignment feature requires more volume. First and second central alignment features 153 and 154 are configured to respectively accommodate and support optical fiber sections 53 and 54 when forming assembly 102.

With reference to FIG. 6A, in various examples monolithic body 110 has an axial length L1 in the range from 7.38 mm to 7.78 mm, back section 124 has a length L2 in the range 1.4 mm to 1.6 mm, and a length L3 of the back section and central section 123 (i.e., from back end 114 to planar end wall 160) is in the range from 4.9 mm to 5.3 mm. Further in the various examples, front section 122 has a length L4 in the range from 2.493 mm to 2.503 mm. Also, monolithic body 110 has maximum width W1 at front end 112 that can be in the range from 0.837 mm to 0.860 mm, and has a width W2 at back end 114 that can be in the range from 0.42 mm to 0.62 mm. The values for these parameters are exemplary and other values and ranges are possible, depending on the particular application.

Figure 7A:
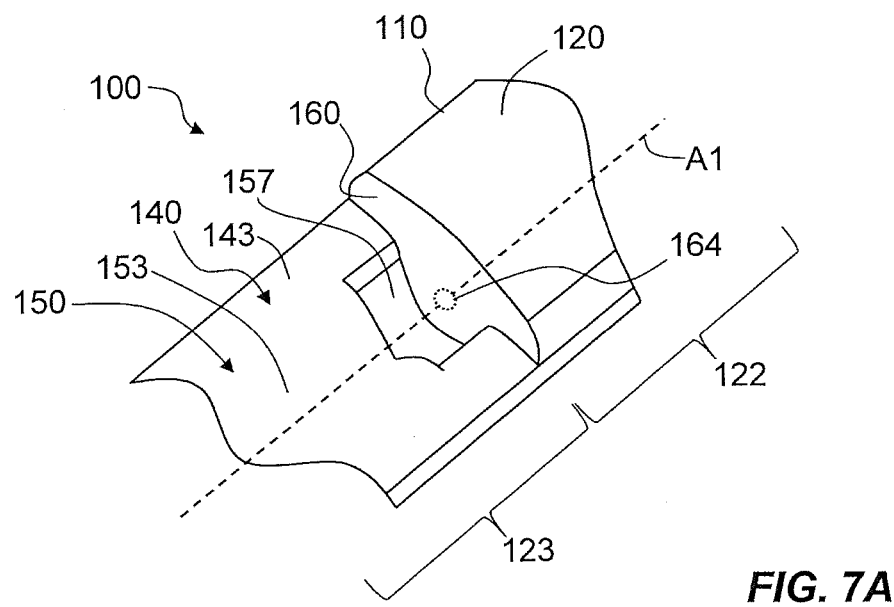
FIG. 7A is a close-up elevated view of the central section of the beam-shaping optical system that shows the end wall and the adjacent recess.
Figure 7B:
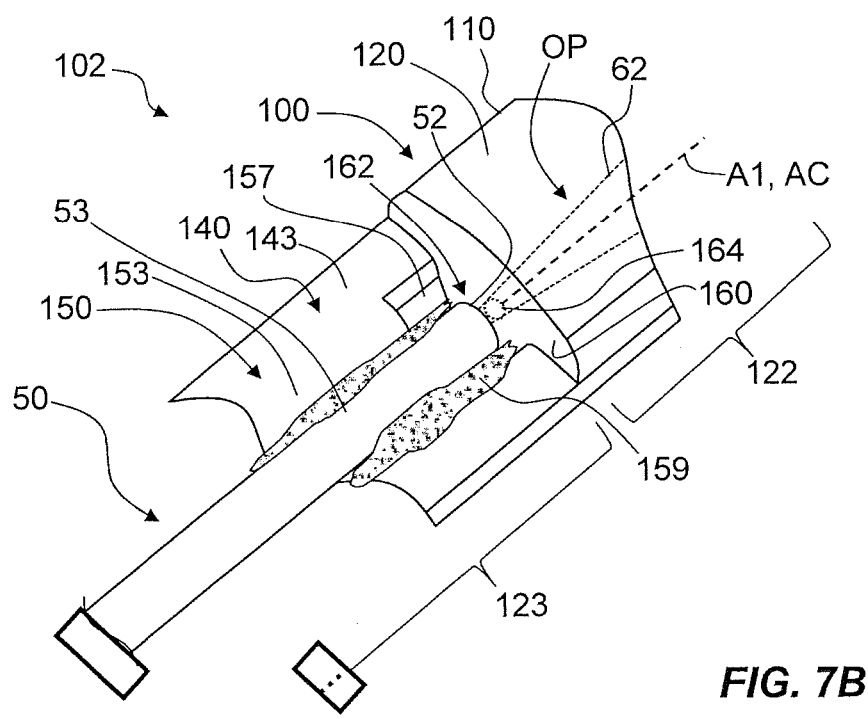
FIG. 7B is similar to FIG. 7A and includes the uncoated optical fiber section operably supported in the second central alignment feature, with the end of the uncoated optical fiber section being adjacent the planar end wall.

FIG. 7A is a close-up elevated view of central section 123 of beam-shaping optical system 100, while FIG. 7B is similar to FIG. 7A and includes uncoated section 53 of optical fiber 50 operably supported in first central alignment feature 153 to form assembly 102. In an example, first central alignment feature 153 includes a recess 157 that terminates at planar end wall 160, which defines the transition between central section 123 and front section 122 of monolithic body 110. The planar end wall 160 defines a portion of outer surface 120 of monolithic body 110.

In an example, end wall 160 has an angle θ1 relative to the vertical (i.e., the Y-direction) (see FIG. 6A). This angle serves to mitigate deleterious effects of reflections of light 62 back into optical fiber 50 from planar end wall 160. In an example, optical fiber end 52 also has an angle, which in an example is the same as angle θ1 of planar end wall 160. This can be accomplished, for example, by precision fiber cleaving techniques. A suitable angle θ1 is defined to be at least as great as needed to avoid light 62 emanating from optical fiber end 52 and reflecting from end wall 160 from re-entering optical fiber 50. Example angles θ1 are usually in the range from about 4° to about 10°, with 8° being an example angle θ1 considered below in the example optical design (see Table 1). As discussed above, optical fiber end 52 can also be angled in like fashion to avoid light 62 reflecting from planar end wall 160 and then reflecting from the optical fiber end face back toward the planar end wall.

The recess 157 serves as a relief feature that facilitates the formation of planar end wall 160 during the molding process. Without recess 157, there is a tendency for end wall 160 to be slightly distorted from the buildup of stress during the molding process, which can result in the end wall being curved and thus having undesirable optical power. Also, as shown in FIG. 7B, recess 157 can be used to accommodate an index-matching material (IMM) 159 that can be used to fix uncoated optical fiber section 53 within first central alignment feature 153. In addition, recess 157 can be used to ensure that optical path OP between the optical fiber end 52 and planar end wall 160 (see FIG. 6D) remains uninterrupted. Likewise, recess 157 can collect any bonding material such as the aforementioned IMM 159 that is used to secure optical fiber 50 to monolithic body 110 but that is not intended to reside between optical fiber end 52 and planar end wall 160.

In an example, optical fiber end 52 resides substantially immediately adjacent planar end wall 160, as shown in FIG. 6C. In the example configuration shown in FIG. 6D, optical fiber end 52 is axially spaced apart from end wall 160 by an axial distance δz to form a gap 162. In the example configuration of FIG. 6D, the axial distance δz is greater than a gap length L5, and gap 162 is filled with IMM 159, which also fills recess 157. In an example, IMM 159 has an adhesive property and is used to secure optical fiber 50 to monolithic body 110. In an example, axial distance δz can be in the range 0≤δz≤1 mm. Thus, in an example, optical path OP travels through IMM 159 disposed between optical fiber end 52 and end wall 160.

Figure 6E:
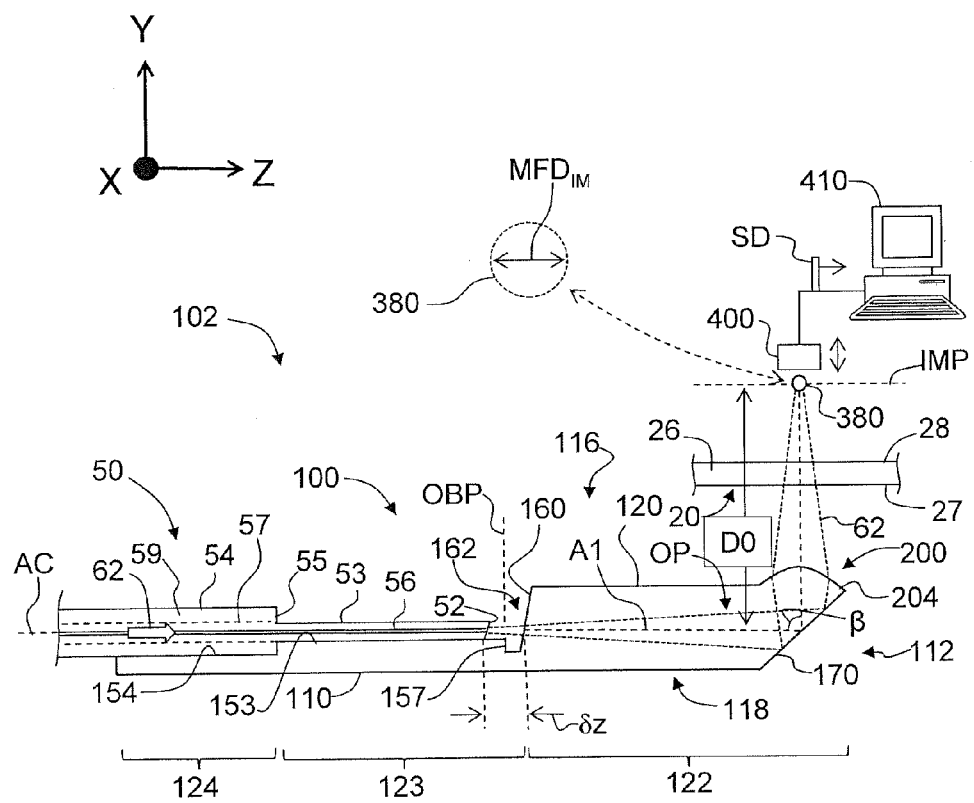
FIG. 6E is similar to FIG. 6D, except that there is no index-matching material between the optical fiber end and the planar end wall.

FIG. 6E is similar to FIG. 6D, except that there is no IMM 159 between optical fiber end 52 and planar end wall 160, which leaves an air gap 162. The air gap 162 can be relatively large (e.g., δz=1 mm). This configuration has the advantage that light 62 does not need to travel through as much optical material. This has the benefit that light 62 is less likely to encounter imperfections (e.g., striae) in the optical material that can scatter or absorb light. Generally, less optical material in the optical path means increased optical transmission.

In addition, the area of the light beam formed by light 62 on planar end wall 160 increases as the square of the increase in distance δz, and can thus be made much larger than the mode-field diameter at optical fiber end 52. This approach can be used to substantially reduce the optical intensity at planar end wall 160 and over optical path OP within body 110. In an example, the reduction in intensity can be many orders of magnitude. This allows for transmitting relatively large amounts of optical power through body 110 without causing material damage to the body.

FIG. 7A shows on end wall 160 a dotted-line circle 164 that represents the clear aperture associated with the planar end wall being the first optical surface of system 100. In other words, dotted-line circle 164 represents the lateral extent of diverging light 62 exiting optical fiber end 52 as it passes through end wall 160 (see FIG. 7B). In an example embodiment, the fiber mode-field diameter $MFD_F$ at optical fiber end 52 is 10 microns at the $1/e^2$ intensity threshold. In an example, gap 162 is included (i.e., δz is intentionally made to be non-zero) so that the intensity of light 62 is reduced by the time it reaches end wall 160 due to the divergence of this light as it exits optical fiber end 52 and travels the distance δz to planar end wall 160. This configuration, an example of which is illustrated in the aforementioned FIG. 6E, reduces the chances of light-induced damage to the portion of monolithic body 110 that supports optical path OP.

With particular reference to the side and cross-sectional views of FIG. 6A and FIG. 6B respectively, front section 122 includes at front end 112 an end wall 170. In an example, end wall 170 is planar and has an angle θ2 as measured with respect to the horizontal (Z-direction). The end wall 170 defines an integrally formed total-internal reflection (TIR) surface, and so is referred to hereinafter as TIR surface 170. The use of integrally formed TIR surface 170 obviates the need for a true (i.e., non-TIR) reflective optical component, such as a silvered mirror or multi-layer coated mirror. The TIR surface 170 constitutes part of outer surface 120 of monolithic body 110. The angle θ2 need not be 45° and in an example can vary by 10° on either side of 45°. The angle θ2 serves to define the fold angle β of folded optical axis A1. In an example discussed below, TIR surface 170 is curved rather than planar and so has an amount of optical power. It is also noted that the reflective surface may be formed by other means, for example, by applying a reflective coating to a planar or a curved surface that is integrally formed as a part of this component.

The front section 122 also includes a lens surface portion 200 integrally formed adjacent front end 112 and end wall 170 at top 116. The lens surface portion 200 includes a lens surface 204 that in an example embodiment has an anamorphic aspherical shape (i.e., is an "anamorphic asphere"). In other words, in such a case lens surface 204 has two different aspheric curvatures in orthogonal X- and Z-directions, as opposed to a rotationally symmetric asphere that has a single aspheric curvature that is the same in all directions. The anamorphic example of lens surface 204 is configured to substantially compensate for asymmetrical optical power of cylindrical housing body 26 that resides in optical path OP, as explained in greater detail below. The lens surface 204 constitutes part of outer surface 120 of monolithic body 110 on top 116 of the monolithic body.

The front section 122 of monolithic body 110 thus includes an optical element having three optical surfaces all integrally formed as part of monolithic body 110: planar end wall 160, TIR surface 170 and lens surface 204. In an example, lens surface 204 is the only optical surface having optical power, i.e., lens surface 204 defines the total optical power for system 100. The portion of monolithic body 110 between planar end wall 160 and lens surface 204 supports a portion of optical path OP traveled by light 62, as well as by scattered light 62S generated in sample 70 and that travels in the opposite direction, as discussed in greater detail below. In other embodiments, the total optical power of the optical element is divided between TIR surface 170 and lens surface 204. In the case where lens surface 204 is the only optical surface having optical power, this surface substantially defines the locations of image plane IMP and object plane OBP. In the case where lens surface 204 and TIR surface 170 each have optical power, then both of these surfaces define the locations of image plane IMP and object plane OBP.

Moreover, as discussed above, monolithic body 110 has a substantially uniform refractive index at the operating wavelength so that there is no optical power within the monolithic body because there is no substantial refractive index gradient.

In an example, lens surface 204 is configured to account for monolithic body 110 being contained within the aforementioned cylindrical transparent housing 20 when forming an OCT probe. In another example, both TIR surface 170 and lens surface 204 are configured to account for monolithic body 110 being contained within the aforementioned cylindrical transparent housing 20 when forming an OCT probe.

The relevant portion of housing 20 is shown in FIG. 4A, FIG. 4B, FIG. 6C and FIG. 6D. Because transparent housing 20 acts as a cylindrical lens element with negative optical power in one direction (i.e., the X-direction) and no optical power in the orthogonal direction (i.e., the Z-direction), lens surface 204 (or both TIR surface 170 and the lens surface) requires asymmetric aberration correction. In the example where all the optical power of system 100 resides in lens surface 204, there needs to be different amounts of optical power (or radii) in the X-direction and the Z-direction.

Moreover, when lens surface 204 contains all the optical power, it is the only optical surface that can be used to correct for optical aberrations to form a suitable image spot 380 at image plane IMP. Thus, in addition to system 100 being corrected for the presence of cylindrical transparent housing 20, in an example lens surface 204 is configured to correct for (i.e., reduce the amount of) spherical aberration that otherwise would substantially degrade the quality of image spot 380 formed at image plane IMP.

The combination of balancing the optical power in different directions and reducing the spherical aberration allows for image spot 380 to be substantially rotationally symmetric, which is advantageous for OCT applications.

Table 1 below sets forth optical design parameters for an example system 100. All distances and curvature amounts in Table 1 are in millimeters. The notation "S/IM" stands for "surface or intervening medium," i.e., an optical surface or an intervening medium between adjacent optical surfaces or between the first optical surface and the object plane OBP or the last optical surface and the image plane IMP. Note that in the example, IMM 159 resides in gap 162 of axial thickness δz between optical fiber end 52 and end wall 160.

Note also that the design parameters treat the system as unfolded and thus as a purely a transmission system with no reflective surface. Such treatment of a folded optical system is commonly used to simplify the description by using a single coordinate system.

The parameter $\theta_S$ stands for the surface angle relative to optical axis A1 and is measured in degrees. Note that $\theta_S$ for planar end wall 160 is given by $\theta_S=90°-\theta 1$, since angle $\theta 1$ is shown in FIG. 6A as being measured relative to the vertical. The parameter TH (mm) stands for the axial thickness as measured between two adjacent optical surfaces or between the first optical surface and the object plane OBP or the last optical surface and the image plane IMP. The parameters $R_x$ and $R_y$ stand for the radii of curvatures in the X and Y directions, respectively. It is noted here that the radii $R_x$ and $R_y$ for lens surface 204 in Table 1 (and also in Table 2) would be $R_x$ and $R_z$ in the folded coordinate system. The parameters $A_x$ and $A_y$ are aspheric coefficients in the X and Y directions, respectively. The surface shape z(x,y) of anamorphic aspheric surface 204 is defined by the following equations:

$$z = \frac{(1/R_x)x^2 + (1/R_y)y^2}{1 + \sqrt{1 - (1/R_x)^2 x^2 - (1/R_x)^2 y^2}} + A_y((1-A_x)x^2 + (1+A_x)y^2)^2$$

$R_x$ is the radius in the X direction (mm)
$R_y$ is the radius in the Y direction (mm)
$A_x$ is the aspheric coefficient in the X direction
$A_y$ is the aspheric coefficient in the Y direction

TABLE 1

Example optical system design parameters

| S/IM | $\theta_S$ | TH | Material | $R_x$ | $R_y$ | $A_x$ | $A_y$ |
|---|---|---|---|---|---|---|---|
| 52 = OBP | 82 | — | — | ∞ | ∞ | — | — |
| 162 | 0 | 0.02 | IMA | ∞ | ∞ | — | — |
| 160 | 82 | 2.503 | ZEONOR | ∞ | ∞ | — | — |
| 170 | 40.1 | .512 | ZEONOR | ∞ | ∞ | — | — |
| 204 | 0 | 0.23 | Air | 0.719 | 0.872 | −0.732 | −.1098 |
| 27 | 0 | 0.2 | Plastic | 0.7 | — | — | — |
| 28 | 0 | 12.6 | Air | 0.9 | — | — | — |
| IMP | 0 | — | Air | ∞ | ∞ | — | — |

Example dimensions L1, L2 and L3 for monolithic body 110 of the present example can be L1=7.58 mm, L2=1.5 mm and L3=4.89 mm. The length L4 is defined by the optical design parameters and in the present example L4=2.503 mm. An example range for length L5 is 0.21 mm to 0.26 mm. Example widths W1 and W2 are W1=0.842 mm and W2=0.52 mm. The object-side numerical aperture $NA_{OBJ}=0.14$, while the image-side $NA_{IM}=0.021$. The example lens surface 204 defines a total optical power for system 100 of 0.565 $mm^{-1}$ in the Z-direction and 0.686 $mm^{-1}$ in the X-direction and defines a system magnification of −6.6.

With reference to FIG. 6C and assembly 102 therein, light 62 that travels within optical fiber 50 exits end 52 and diverges as it passes through gap 162 and IMM 159 therein and then through planar end wall 160, which has an angle θ1=8° (i.e., $\theta_S$=82°). The light 62 continues to diverge as it travels through monolithic body 110 of front section 122 and reflects from TIR surface 170, which has an angle θ2=40.1°. The light 62 that reflects from TIR surface 170 then passes through lens surface 204, which causes the light to converge non-uniformly due to this surface being anamorphic. This non-uniformly converging light 62 passes through a portion of housing body 26, which, as discussed above, acts as a cylindrical meniscus lens with negative optical power.

The combined effects of housing body 26 and lens surface 204 are such that image spot 380 formed at image plane IMP is substantially rotationally symmetric and tightly focused. For example, for a fiber $\text{MFD}_F$=10 μm at the $1/e^2$ intensity threshold, at image plane IMP the corresponding image $\text{MFD}_{IM}$=66 μm at the $1/e^2$ intensity threshold. The image plane IMP and image spot 380 are located at a distance D=13.5 mm from the horizontal portion of optical axis A1. The clear apertures associated with optical surfaces 160, 170 and 204 are designed to prevent vignetting. The operating wavelength of the example system 100 is λ=1,300 nm. For the example system 100, the clear aperture at TIR surface 170 is 900 μm in the Y-direction and is 725 μm in the X-direction. The clear aperture of lens surface 204 is 700 μm diameter.

In an example embodiment of system 100, a reflective surface (TIR surface) 170 is also curved and so has optical power, so that the total optical power of system 100 is defined by the optical power from the TIR surface and lens surface 204. In this case, TIR surface 170 and lens surface 204 are configured to substantially compensate for asymmetrical optical power of cylindrical housing body 26 of housing 20 that resides in optical path OP.

Figure 6F:
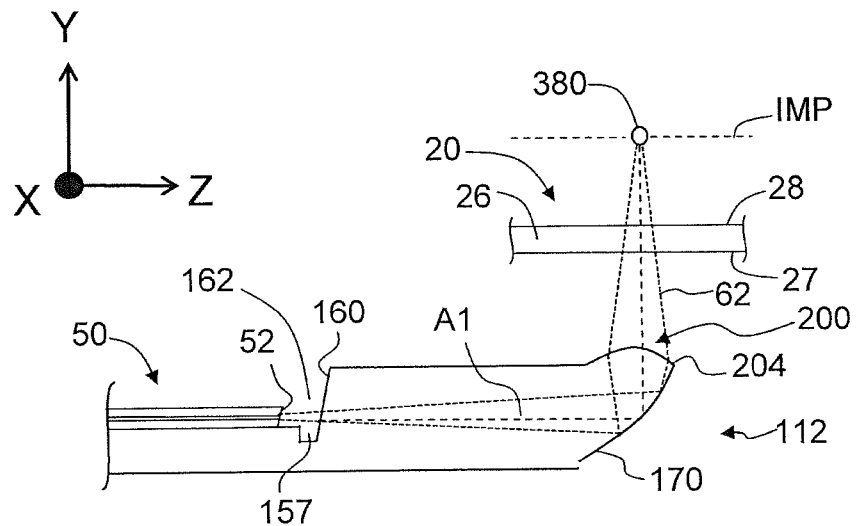
FIG. 6F and FIG. 6G are cross-sectional close-up views of the front end of the beam-shaping optical system as taken in the Y-Z plane, wherein both the TIR surface and the lens surface have optical power.
Figure 6G:
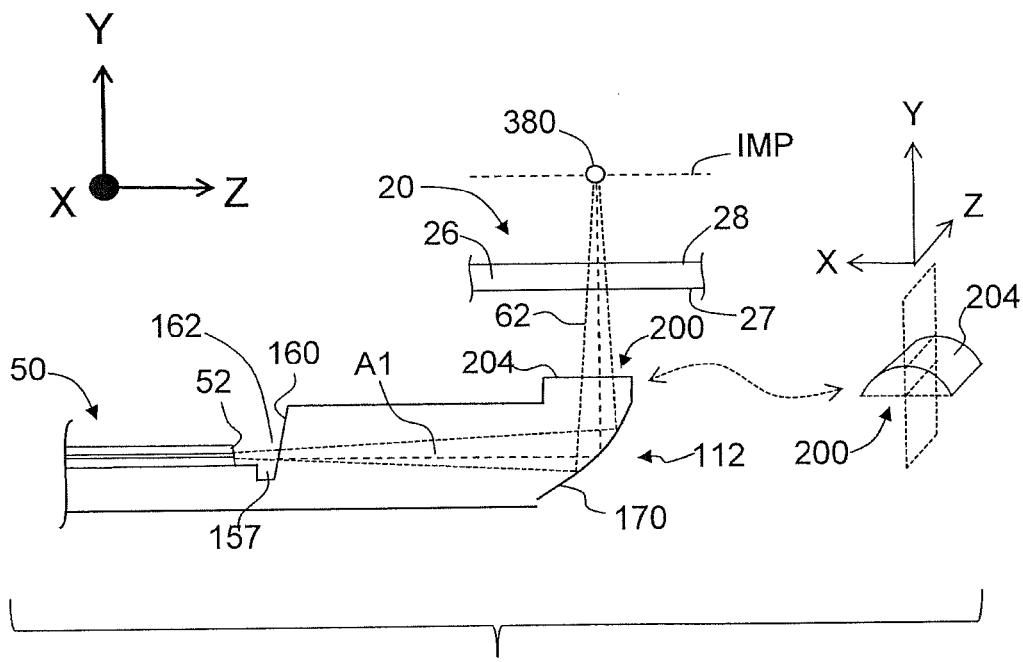

In one example embodiment shown in FIG. 6F, TIR surface 170 and lens surface 204 have power in both the Y-Z and X-Z planes, respectively. In another example embodiment illustrated in FIG. 6G, TIR surface 170 and lens surface 204 are cylindrical surfaces with optical power in orthogonal planes. FIG. 6G includes an inset that shows lens surface 204 as a cylindrical lens with curvature in the X-Y plane.

The system of FIG. 6E could also represent this case, wherein the reflective (TIR) surface 170 has cylindrical curvature in the X-Z plane and lens surface 204 has cylindrical curvature in the Y-Z plane. The TIR surface 170 and lens surface 204 can be either spherical or aspherical surfaces.

Thus, in one example of system 100, only lens surface 204 has optical power and is configured to substantially compensate for the asymmetric optical power of OCT transparent housing 20. In another example of system 100, lens surface 204 and TIR surface 170 have optical power and are cooperatively configured to substantially compensate for the asymmetric optical power of OCT transparent housing 20.

Table 2 below sets forth example optical system design parameters for the example system 100 wherein the optical power is shared between TIR surface 170 and lens surface 204 and wherein the system is treated as an unfolded transmission system for ease of expressing the optical design parameters in a single coordinate system where optical axis A1 is in the Z-direction. As in Table 1, TH, $R_x$ and $R_y$ are in millimeters.

TABLE 2

Example optical system design parameters

| Surface # | $\theta_S$ | TH | Material | $R_x$ | $R_y$ |
|---|---|---|---|---|---|
| 52 = OBP | 82 | — | — | ∞ | ∞ |
| 162 | 82 | 0.02 | adhesive | ∞ | ∞ |
| 160 | 82 | 2.75 | ZEONOR | ∞ | ∞ |
| 170 | 49.9 | 0.50 | ZEONOR | 2.63 | ∞ |
| 204 | 0 | 0.20 | Air | ∞ | 0.935 |
| 27 | 90 | 0.2 | Plastic | 0.7 | — |
| 28 | 90 | 12.6 | Air | 0.9 | — |
| IMP | 90 | — | Air | ∞ | ∞ |

The example system 100 as set forth in Table 2 has TIR surface 170 and lens surface 204 as spherical cylindrical surfaces with optical powers in orthogonal planes.

System Advantages

Because system 100 has monolithic body 110, the system has no need for the use of spacers, GRIN lenses or separate non-TIR reflective surfaces. Further, eliminating the use of multiple optical components is beneficial because there are fewer material interfaces from which detrimental optical back reflections can occur. In addition, the use of first and second central alignment features 153 and 154 facilitates strain relief for optical fiber 50 when forming assembly 102.

The proper alignment of optical fiber 50 within system 100 when forming assembly 102 is facilitated by the use of first and second central alignment features 153 and 154. With reference to FIG. 6C through FIG. 6E, in an example method for achieving optical fiber alignment, a photodetector 400 can be used to capture at least one image of image spot 380 and generate a detector signal SD representative of the captured image. The captured image(s) can be analyzed, e.g., via a computer 410 that is operably connected to photodetector 400. The computer 410 can be used to analyze and display information about the captured image spot(s) 380. In an example, a plurality of image spots 380 are detected through focus and compared to the corresponding reference spots (e.g., as obtained via optical modeling based on the optical design of system 100) to assess performance.

It is noted that the section of housing 20 shown can be represented by a cylindrical lens portion during testing rather than using an entire housing 20.

The position of optical fiber 50 can be axially adjusted within the first and second central alignment features 153 and 154 based on making one or more measurements of image spot 380 until an acceptable or optimum image spot 380 is formed. In an example, the one or more measured image spots 380 are compared to a reference image spot or a reference image spot size. The optical fiber 50 can then be fixed in its aligned position within first and second central alignment features 153 and 154 using, for example, IMM 159 as discussed above. In an example, coated section 54 of optical fiber 50 can be fixed (e.g., bonded) within second central alignment feature 154 to provide strain relief.

Figure 8:
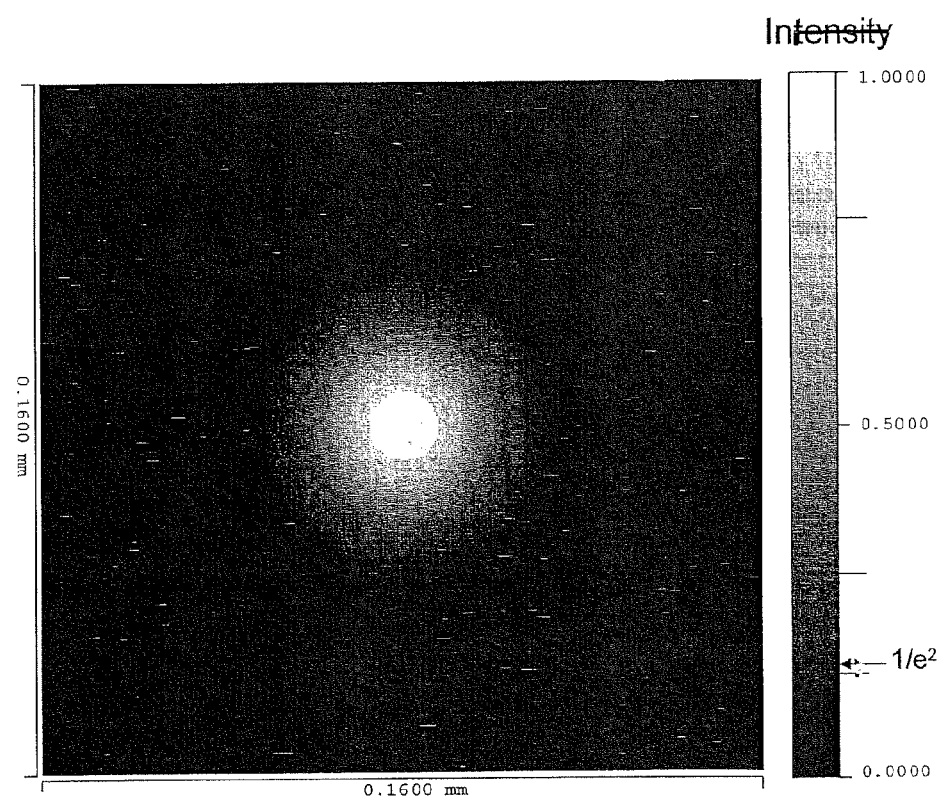
FIG. 8 is a simulated example image spot based on the example optical system of Table 1, and shows the spot's general rotational symmetry and the image $MFD_{IM}$ of about 66 μm.

FIG. 8 is a simulated image of image spot 380 for the example system 100 set forth in Table 1. The normalized intensity is shown in gray scale in the right-hand legend. The image $\text{MFD}_{IM}$ of about 66 μm is shown, with the $1/e^2$ intensity threshold being approximated.

Figure 9:
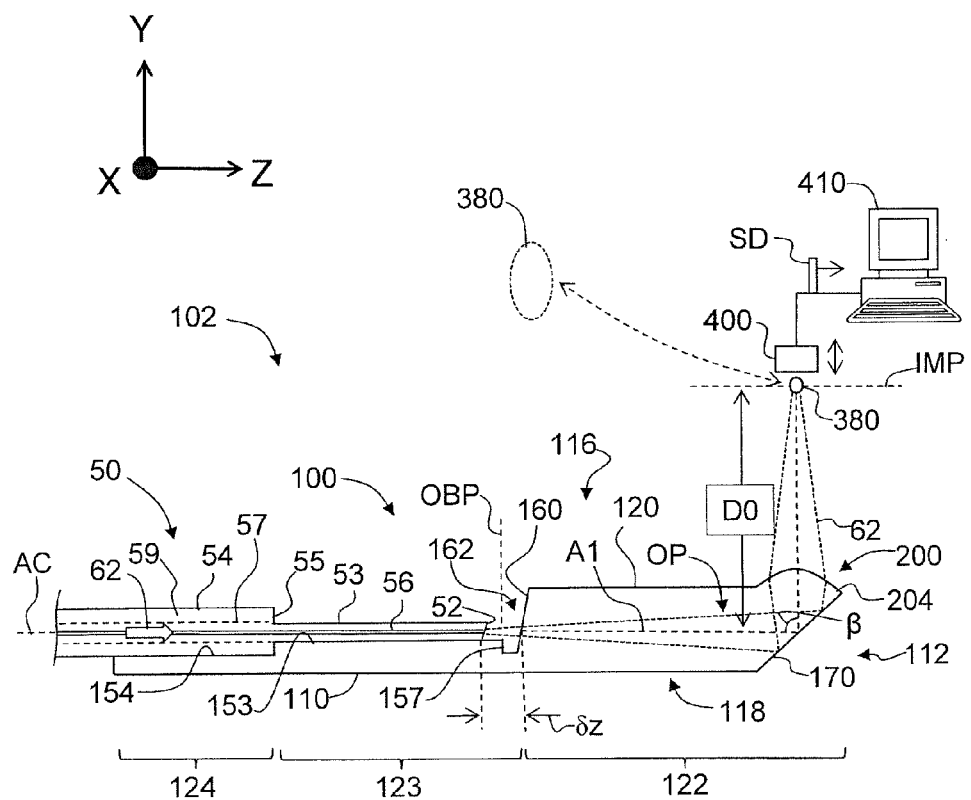
FIG. 9 is similar to FIG. 6E and illustrates an example embodiment wherein the cylindrical transparent housing (or its equivalent cylindrical lens) is not present in the optical path so that the beam-shaping optical system can be optically tested.

FIG. 9 is similar to FIG. 6E and illustrates an example method for achieving optical fiber alignment while also optically testing system 100. In FIG. 9, the section of housing 20 (or the equivalent cylindrical lens element) is removed and the image spot 380 is detected. In this case, image spot 380 will not be rotationally symmetric such as shown in FIG. 8 but will be distorted, e.g., will appear elliptical, as shown in inset of FIG. 9. In an example, the image spot is detected at different focus positions to establish the characteristics of the image spot through focus. The captured image or images are then compared to the corresponding reference image spot(s) or a reference image spot size(s). If the best measured image spots fail to measure up to the reference image spots (which can be modeled based on the optical design data for system 100), then it can be concluded that system 100 does not meet specification, barring any alignment issues.

In an example embodiment, the method of testing system 100 includes optimizing the axial alignment of optical fiber 50 by axially adjusting its position so that image spot 380 most closely matches the reference image spot.

Figure 10:
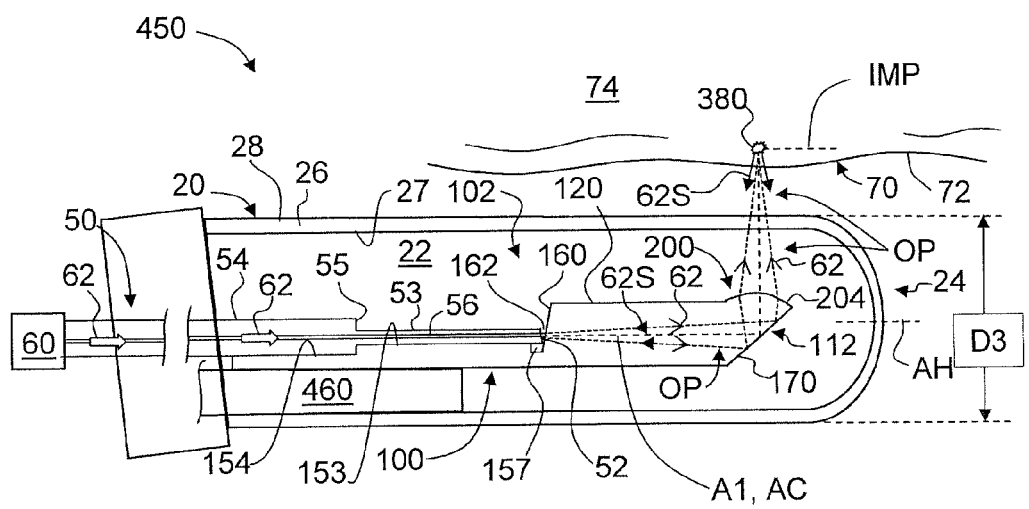
FIG. 10 is similar to FIG. 6B and shows the beam-shaping optical assembly as contained within a transparent cylindrical housing to form an OCT probe according to the disclosure.

FIG. 10 is similar to FIG. 6B and shows assembly 102 contained within housing 20 to form an OCT probe 450 according to the disclosure. In an example, a rotatable support fixture 460 is used to hold system 100 within housing interior 22 with optical axis A1 and housing axis AH being either substantially collinear or slightly offset but parallel to one another. The housing 20 has an outer diameter D3 that in an example is in the range from 1 mm to 2 mm. The housing 20 resides in the optical path OP between lens surface 204 and image plane IMP. Rotatable support fixture 460 is configured to rotate system 100 within housing interior 22 using techniques known in the art, such as shown in more detail in the aforementioned U.S. Patent Application Publication No. 2009/0198125.

FIG. 11 and FIG. 12 are cross-sectional views of OCT probe 450 of FIG. 10 as taken in the X-Y plane and the Y-Z plane, respectively. These Figures illustrate how image spot 380 is formed at a single image plane IMP at a distance D0 from (horizontal) optical axis A1 even though converging light 62 passes through cylindrically curved housing 20, which resides in the optical path OP between lens surface 204 and image plane IMP. Likewise, scattered light 62S from sample 70 (see FIG. 10) travels from the sample to optical fiber 50 over substantially the same optical path OP and is imaged onto optical fiber end 52 with high imaging quality.

Figure 13:
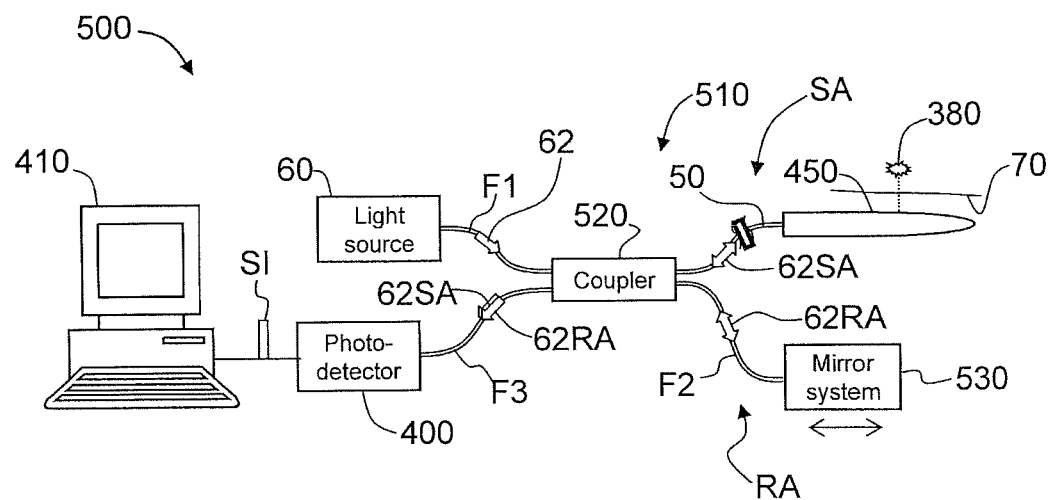
FIG. 13 is a schematic diagram an example OCT system that includes the OCT probe as disclosed herein.

FIG. 13 is a schematic diagram of an example OCT system 500 that includes OCT probe 450 as disclosed herein. OCT system 500 includes light source 60 and an interferometer 510. Light source 60 is optically connected to a fiber optic coupler ("coupler") 520 via a first optical fiber section F1. OCT probe 450 is optically connected to coupler 520 via optical fiber 50 and constitutes the sample arm SA of an interferometer. OCT system 500 also includes a mirror system 530 optically connected to coupler 520 via an optical fiber section F2. Movable mirror 5230 and optical fiber section F2 constitute a reference arm RA of the interferometer. Mirror system 530 is configured to alter the length of the reference arm, e.g., via a movable mirror (not shown). OCT system 500 further includes a photodetector 400 optically coupled to coupler 520 via a third optical fiber section F3. Photodetector 400 in turn is electrically connected to computer 410.

In operation, light source 60 generates light 62 that travels to interferometer 520 over optical fiber section F1. The light 62 is divided by coupler 520 into light 62RA that travel in reference arm RA and light 62SA that travels in sample arm SA. The light 62RA that travels in reference arm RA is reflected by mirror system 530 and returns to coupler 520, which directs the light to photodetector 400. The light 62SA that travels in sample arm SA is processed by OCT probe 450 as described above (where this light was referred to as just light 62) to form light spot 380 on or in a sample 70. The resulting scattered light (see scattered light 62S of FIG. 10) is collected by OCT probe 450 and directed through optical fiber 50 to coupler 520, which directs it (as light 62SA) to photodetector 400. The reference arm light 62RA and sample arm light 62SA interfere and the interfered light is detected by photodetector 400. Photodetector 400 generates an electrical signal SI in response thereto, which is then sent to computer 410 for processing using standard OCT signal processing techniques.

The optical interference of light 62SA from sample arm SA and light 62RA from reference arm RA is detected by photodetector 400 only when the optical path difference between the two arms is within the coherence length of light 62 from light source 62. Depth information from sample 70 is acquired by axially varying the optical path length of reference arm RA via mirror system 530 and detecting the interference between light from the reference arm and scattered light from the sample arm that originates from within the sample. A three-dimensional image is obtained by transversely scanning in two dimensions the optical path in the sample arm. The axial resolution of the process is determined by the coherence length.

Thus, according to at least some embodiments, a beam-shaping optical system that supports an optical fiber having a central axis and an end, with the system being suitable for use within an optical coherence tomography (OCT) transparent housing having a cylindrical body with asymmetric optical power, comprises: (i) a transparent monolithic body having an optical axis, an outer surface and opposite front and back ends, with the transparent monolithic body having formed integrally therewith in order along the optical axis from the back end; (ii) at least one alignment feature configured to operably support the optical fiber so that the optical fiber central axis is substantially coaxially aligned with the optical axis; (iv) a surface (e.g., total-internal-reflection (TIR)) at the front end that forms the folded optical axis; and (v) a lens surface integrally formed in the monolithic body along the folded optical axis and constituting part of the outer surface adjacent the front end; and wherein the transparent housing has surfaces that are configured to substantially compensate for the asymmetric optical power of the OCT transparent housing.

Thus, according to some embodiments, a beam-shaping optical system that supports an optical fiber having a central axis and an end, with the system being suitable for use within an optical coherence tomography (OCT) transparent housing having a cylindrical body with asymmetric optical power, comprises: (i) a transparent monolithic body having an optical axis, an outer surface and opposite front and back ends, with the transparent monolithic body having formed integrally therewith in order along the optical axis from the back end; (ii) at least one alignment feature configured to operably support the optical fiber so that the optical fiber central axis is substantially coaxially aligned with the optical axis; (iii) a recess that terminates the at least one alignment feature at an angled planar end wall; (iv) a reflective (e.g., total-internal-reflection (TIR) surface) at the front end that forms the folded optical axis; and (v) a lens surface integrally formed in the monolithic body along the folded optical axis and constituting part of the outer surface adjacent the front end; and wherein either: (a) only the lens surface has optical power and is configured to substantially compensate for the asymmetric optical power of the OCT transparent housing; or (b) the lens surface and the reflective surface (i.e., TIR surface) each have optical power and are cooperatively configured to substantially compensate for the asymmetric optical power of the OCT transparent housing. The reflective surface, such as the TIR surface, may be planar, or may have has a cylindrical curvature. According to some embodiments the lens surface has an anamorphic aspherical shape. According to some embodiments, the monolithic body has an axial length L1 in the range from 1.4 mm to 1.6 mm and a width W1 in the range from 0.83 mm to 0.85 mm. According to some embodiments, the monolithic transparent body is transparent over an operating wavelength in the range from 700 nm to 1,600 nm. The monolithic body may consists of either a polymer material, a plastic material, or a glass. For example, the monolithic transparent body may be made of polymer material, preferably ZEONOR®.

According to some embodiments, the optical fiber includes a coated section and an uncoated section, and the at least one alignment feature comprises first and second grooves formed in first and second flat surfaces, with the first and second grooves respectively sized to accommodate the coated and uncoated sections. According to some embodiments, the optical fiber is operably supported by the at least one alignment feature. According to some embodiments, the optical has an angled end that resides adjacent the angled planar end wall.

According to some embodiments, an index-matching material is disposed between the angled optical fiber end and the angled planar end wall. According to some embodiments, an index-matching material is disposed between the angled optical fiber end and the angled planar end wall wherein the optical fiber angled end resides at a distance δz from the angled planar end wall, wherein δz is in the range $0 \leq \delta z \leq 1$ mm.

According to some embodiments, an optical coherence tomography (OCT) system, comprises: an OCT probe that includes any of the beam-shaping optical systems described herein; a light source that emits light coherent light; an interferometer optically coupled to the light source, the interferometer having a reference arm and a sample arm, wherein the sample arm includes the OCT probe, with the interferometer being configured to cause light to travel over both the sample and reference arms and to formed interfered light; a photodetector configured to receive and detect the interfered light and to generate an electrical signal in response thereto; and a computer configured to receive and process the electrical signal.

According to some embodiments an optical coherence tomography (OCT) system, and that is for use within a transparent cylindrical housing that has asymmetric optical power, comprises: an OCT probe including a transparent monolithic body having a substantially uniform refractive index at an infrared operating wavelength, a folded optical axis, a top, a front end and a back end and an outer surface, with the outer surface having at least one flat surface that is formed in the top and that is adjacent the back end;

at least one alignment feature integrally formed in the at least one flat surface of the monolithic body and configured to support and align the optical fiber, the at least one alignment feature terminating at an end wall that defines a first optical surface;

a surface (for example, TIR) surface formed in the monolithic body at the front end and along the optical axis, the surface being angled relative to the optical axis and defining a second optical surface that forms the folded optical axis; and a lens surface formed on the top of the monolithic body adjacent the front end and along the folded optical axis, the lens surface constituting part of the outer surface and defining a third optical surface having an anamorphic aspherical shape and that defines an optical power for the beam-shaping optical system that substantially compensates for the asymmetric optical power of the cylindrical housing at least partially surrounding the OCT probe.

According to some embodiments a beam-shaping optical system that supports an optical fiber and that is for use within a transparent cylindrical housing that has asymmetric optical power, comprises:

a transparent monolithic body having a substantially uniform refractive index at an infrared operating wavelength, a folded optical axis, a top, a front end and a back end and an outer surface, with the outer surface having at least one flat surface that is formed in the top and that is adjacent the back end;

at least one alignment feature integrally formed in the at least one flat surface of the monolithic body and configured to support and align the optical fiber, the at least one alignment feature terminating at an angled planar end wall that defines a first optical surface;

a recess formed in the at least one optical fiber alignment feature adjacent the angled planar end wall;

a total-internal reflection (TIR) planar surface integrally formed in the monolithic body at the front end and along the optical axis, the TIR planar surface being angled relative to the optical axis and defining a second optical surface that forms the folded optical axis; and a lens surface formed on the top of the monolithic body adjacent the front end and along the folded optical axis, the lens surface constituting part of the outer surface and defining a third optical surface having an anamorphic aspherical shape and that defines an optical power for the beam-shaping optical system that substantially compensates for the asymmetric optical power of the cylindrical housing. In some embodiments of this beam-shaping optical system the monolithic body has an axial length L1 in the range from 1.4 mm to 1.6 mm and a width W1 in the range from 0.83 mm to 0.85 mm. According to some embodiments this beam-shaping optical system operates at least one wavelength in the infrared operating wavelength is in 700 nm to 1600 nm range. According to some embodiments of this beam-shaping optical system, the optical fiber includes a coated section and an uncoated section, and further wherein the least one flat surface and the at least one alignment feature include: (a) a first flat surface portion adjacent the angled planar end wall and having formed therein a first central alignment groove sized to accommodate the uncoated section of the optical fiber; and (b) a second flat surface portion between the back end and the first flat surface portion, the second flat surface portion having formed therein a second central alignment groove sized to accommodate the coated section of the optical fiber, and wherein the second flat surface portion is elevated relative to the first flat surface portion. According to some embodiments of this beam-shaping optical system, the optical fiber includes a coated-section edge that defines a boundary between the coated and uncoated sections, and wherein the first and second central alignment grooves define an alignment feature edge against which coated-section edge butts when optical fiber is operably arranged in the first and second alignment grooves. According to some embodiments, the monolithic body consists of either a polymer material or a plastic material, and preferably ZEONOR®. According to some embodiments, the beam-shaping optical assembly comprises: the beam-shaping optical system according to any of the embodiments described herein, and the optical fiber operably supported by the at least one alignment feature, wherein the optical fiber has an end that resides adjacent the angled planar end wall and at an object plane defined by the lens surface. According to some embodiments, the optical fiber end is angled.

According to some embodiments, a method of forming an image spot through a cylindrical transparent housing having asymmetric optical power with light from an optical fiber having an end and a central axis, comprises the steps of:

operably supporting the optical fiber in at least one alignment feature of a transparent monolithic body having an outer surface and configured to define a folded optical path along a folded optical axis from an angled planar end wall to a total-internal-reflection (TIR) surface and then to a lens surface, with either the lens surface or the lens surface and the TIR surface defining an object plane at which the optical fiber end resides and an image plane where the image spot is formed, the lens surface constituting part of the outer surface, with either the lens surface or both the lens surface and the TIR surface being configured to substantially compensate for the asymmetric optical power of the cylindrical transparent housing, which lies in the optical path between the lens surface and the image plane; and sending light from the optical fiber end at the object plane through the angled planar end wall and over the folded optical path to the image plane to form a substantially rotationally symmetric image spot at the image plane. According to some embodiments, the TIR surface is a planar surface and the lens surface is an anamorphic aspherical surface. The method may further include a step of disposing the optical fiber end so that it is spaced apart from the angled end wall by a distance δz in the range 0≤δz≤1 mm. According to at least some embodiments the method further includes the step of providing the light with an operating wavelength between 700 nm and 1,600 nm. According to some embodiments, the method includes the step of axially aligning the optical fiber within the at least one alignment feature based on one or more measurements of the image spot. According to some embodiments, the method includes the step of forming the TIR surface and/or the lens surfaces as cylindrical surfaces with optical power in orthogonal directions. According to some embodiments, the optical fiber end and the angled end wall define a gap, and the method further comprise the steps of:

filling the gap with an index-matching material; and
transmitting the light through the index-matching material.

According to some embodiments, a method of optical testing a beam-shaping optical system that defines an object plane and an image plane, comprising: (i) providing the beam-shaping optical system in the form of a transparent monolithic body with an outer surface that has at least one alignment feature and a folded optical path along a folded optical axis from an angled planar end wall to reflective surface and then to a lens surface that constitutes part of the outer surface; (ii) supporting an optical fiber in the at least one alignment feature, the optical fiber having an end, wherein the end resides at an image plane of the beam-shaping optical system; (iii) sending light from the optical fiber end through the angled planar end wall and over the folded optical path to the image plane to form an image spot at an image plane; and (iv) detecting the image spot at the image plane; and (iv) comparing the detected image spot to a reference image spot.

According to some embodiments, a method of optical testing a beam-shaping optical system that defines an object plane and an image plane, comprising: (i) providing the beam-shaping optical system in the form of a transparent monolithic body with an outer surface that has at least one alignment feature and a folded optical path along a folded optical axis from an angled planar end wall to a total-internal-reflection (TIR) surface and then to a lens surface that constitutes part of the outer surface; (ii) supporting an optical fiber in the at least one alignment feature, the optical fiber having an end, wherein the end resides at an image plane of the beam-shaping optical system; (iii) sending light from the optical fiber end through the angled planar end wall and over the folded optical path to the image plane to form an image spot at an image plane; and (iv) detecting the image spot at the image plane; and (iv) comparing the detected image spot to a reference image spot.

According to some embodiments the method of optical testing a the beam-shaping optical system further comprises the step of disposing the beam-shaping optical system in an interior of a transparent cylindrical housing so that the optical path passes through a portion of the transparent cylindrical housing.

According to some embodiments the method of optical testing a the beam-shaping optical system further comprises the step of inserting into the optical path between the lens surface and the image plane a cylindrical optical element having optical power that is representative of a OCT probe transparent cylindrical housing.

According to some embodiments the method of optical testing a the beam-shaping optical system further comprises the steps of: (i) Detecting multiple image spots as a function of focus position; and (ii) Comparing the multiple image spots to corresponding multiple reference image spots.

According to some embodiments the method of optical testing a the beam-shaping optical system further comprises the step of optimizing an axial alignment of the optical fiber by axially adjusting a position of the optical fiber so that the image spot most closely matches the reference image spot.

Although the embodiments herein have been described with reference to particular aspects and features, it is to be understood that these embodiments are merely illustrative of desired principles and applications. It is therefore to be understood that numerous modifications may be made to the illustrative embodiments and that other arrangements may be devised without departing from the spirit and scope of the appended claims.

What is claimed is:

1. A beam-shaping optical system that supports an optical fiber having a central axis and an end, with the system being suitable for use within an optical coherence tomography (OCT) transparent housing having a cylindrical body with asymmetric optical power, comprising:

a transparent monolithic body having an optical axis, an outer surface and opposite front and back ends, with the transparent monolithic body having formed integrally therewith in order along the optical axis from the back end:

at least one alignment feature configured to operably support the optical fiber so that the optical fiber central axis is substantially coaxially aligned with the optical axis;

a recess that terminates the at least one alignment feature at an angled planar end wall, the angled planar end wall is situated to face the end of the optical fiber;

a total-internal-reflection (TIR) surface at the front end that forms the folded optical axis; and a lens surface integrally formed in the monolithic body along the folded optical axis and constituting part of the outer surface adjacent the front end; and wherein either:

a) only the lens surface has optical power and is configured to substantially compensate for the asymmetric optical power of the OCT transparent housing; or
b) the lens surface and the TIR surface each have optical power and are cooperatively configured to substantially compensate for the asymmetric optical power of the OCT transparent housing.

2. The beam-shaping optical system according to claim 1, wherein the TIR surface is planar, or has a cylindrical curvature.

3. The beam-shaping optical system according to claim 2, wherein the lens surface has an anamorphic aspherical shape.

4. The beam-shaping optical system according to claim 1, wherein the monolithic body has an axial length L1 in the range from 1.4 mm to 1.6 mm and a width W1 in the range from 0.83 mm to 0.85 mm.

5. The beam-shaping optical system according to claim 1, wherein the monolithic transparent body is transparent over an operating wavelength in the range from 700 nm to 1,600 nm.

6. The beam-shaping optical system according to claim 1, wherein the optical fiber includes a coated section and an uncoated section, and wherein the at least one alignment feature comprises first and second grooves formed in first and second flat surfaces, with the first and second grooves respectively sized to accommodate the coated and uncoated sections.

7. The beam-shaping optical system according to claim 1, further comprising the optical fiber, wherein the optical fiber is operably supported by the at least one alignment feature.

8. The beam-shaping optical system according to claim 7, further including the optical fiber having an angled end that resides adjacent the angled planar end wall.

9. The beam-shaping optical system according to claim 8, further comprising an index-matching material disposed between the angled optical fiber end and the angled planar end wall.

10. The beam-shaping optical system according to claim 8, wherein the optical fiber angled end resides at a distance $\delta z$ from the angled planar end wall, wherein $\delta z$ is in the range $0 \leq \delta z \leq 1$ mm.

11. The beam-shaping optical system according to claim 1, wherein the monolithic body consists of either a polymer material, a plastic material or a glass.

12. The beam-shaping optical system according to claim 11, wherein the polymer material is ZEONOR®.

13. A beam-shaping optical system that supports an optical fiber having a central axis and an end, with the system being suitable for use within an optical coherence tomography (OCT) transparent housing having a cylindrical body with asymmetric optical power, comprising:
a transparent monolithic body having an optical axis, an outer surface and opposite front and back ends, with the transparent monolithic body having formed integrally therewith in order along the optical axis from the back end:
at least one alignment feature configured to operably support the optical fiber so that the optical fiber central axis is substantially coaxially aligned with the optical axis;
a recess that terminates the at least one alignment feature at an angled planar end wall;
a total-internal-reflection (TIR) surface at the front end that forms the folded optical axis; and
a lens surface integrally formed in the monolithic body along the folded optical axis and constituting part of the outer surface adjacent the front end; and
wherein either:
a) only the lens surface has optical power and is configured to substantially compensate for the asymmetric optical power of the OCT transparent housing; or
b) the lens surface and the TIR surface each have optical power and are cooperatively configured to substantially compensate for the asymmetric optical power of the OCT transparent housing,
wherein the monolithic body consists of either a polymer material, a plastic material or a glass.

14. The beam-shaping optical system according to claim 13, wherein the polymer material is ZEONOR®.

15. A method of forming an image spot through a cylindrical transparent housing having asymmetric optical power with light from an optical fiber having an end and a central axis, comprising:
operably supporting the optical fiber in at least one alignment feature of a transparent monolithic body having an outer surface and configured to define a folded optical path along a folded optical axis from an angled planar end wall to a total-internal-reflection (TIR) surface and then to a lens surface, with either the lens surface or the lens surface and the TIR surface defining an object plane at which the optical fiber end resides and an image plane where the image spot is formed, the lens surface constituting part of the outer surface, with either the lens surface or both the lens surface and the TIR surface being configured to substantially compensate for the asymmetric optical power of the cylindrical transparent housing, which lies in the optical path between the lens surface and the image plane; and
sending light from the optical fiber end at the object plane through the angled planar end wall and over the folded optical path to the image plane to form a substantially rotationally symmetric image spot at the image plane.

16. The method according to claim 15, wherein the TIR surface is a planar surface and the lens surface is an anamorphic aspherical surface.

17. The method according to claim 15, wherein the optical fiber includes a coated section and an uncoated section, wherein the at least one alignment feature includes first and second aligned grooves, and wherein operably supporting the optical fiber in the at least one alignment feature includes operably supporting the coated section in the first groove and operably supporting the uncoated section in the second groove.

18. The method according to claim 15, further comprising:
disposing the optical fiber end so that it is spaced apart from the angled end wall by a distance $\delta z$ in the range $0 \leq \delta z \leq 1$ mm.

19. The method according to claim 18, wherein the optical fiber end and the angled end wall define a gap, and further comprising:
filling the gap with an index-matching material; and
transmitting the light through the index-matching material wherein the light has an operating wavelength between 700 nm and 1,600 nm.

20. The method according to claim 15, further comprising axially aligning the optical fiber within the at least one alignment feature based on one or more measurements of the image spot.

21. The method according to claim 15, further comprising forming the TIR surface and the lens surfaces as cylindrical surfaces with optical power in orthogonal directions.

22. A beam-shaping optical system that supports an optical fiber having a central axis and an end, with the system being suitable for use within an optical coherence tomography (OCT) transparent housing having a cylindrical body with asymmetric optical power, comprising:

a transparent monolithic body having an optical axis, an outer surface and opposite front and back ends, with the transparent monolithic body having formed integrally therewith in order along the optical axis from the back end:

at least one alignment feature configured to operably support the optical fiber so that the optical fiber central axis is substantially coaxially aligned with the optical axis;

a recess that terminates the at least one alignment feature at an angled planar end wall, the angled planar end wall is situated to face the end of the optical fiber;

a reflective surface at the front end that forms the folded optical axis; and a lens surface integrally formed in the monolithic body along the folded optical axis and constituting part of the outer surface adjacent the front end; and wherein either:

a) only the lens surface has optical power and is configured to substantially compensate for the asymmetric optical power of the OCT transparent housing; or b) the lens surface and the reflective surface each have optical power and are cooperatively configured to substantially compensate for the asymmetric optical power of the OCT transparent housing.

\* \* \* \* \*